United States Patent
Amakawa et al.

(10) Patent No.: US 12,343,708 B2
(45) Date of Patent: Jul. 1, 2025

(54) METHOD FOR PRODUCING A CATALYTICALLY ACTIVE MULTI-ELEMENT OXIDE CONTAINING THE ELEMENTS Mo, W, V AND Cu

(71) Applicant: BASF SE, Ludwigshafen am Rhein (DE)

(72) Inventors: Kazuhiko Amakawa, Ludwigshafen am Rhein (DE); Samira Parishan, Ludwigshafen am Rhein (DE); Christian Walsdorff, Ludwigshafen am Rhein (DE); Patrick Hubach, Ludwigshafen am Rhein (DE); Tobias Weinland, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 375 days.

(21) Appl. No.: 17/918,345

(22) PCT Filed: Apr. 12, 2021

(86) PCT No.: PCT/EP2021/059382
§ 371 (c)(1),
(2) Date: Oct. 12, 2022

(87) PCT Pub. No.: WO2021/213823
PCT Pub. Date: Oct. 28, 2021

(65) Prior Publication Data
US 2023/0144424 A1    May 11, 2023

(30) Foreign Application Priority Data
Apr. 21, 2020 (EP) .................................. 20170533

(51) Int. Cl.
B01J 23/888 (2006.01)
B01J 6/00 (2006.01)
(Continued)

(52) U.S. Cl.
CPC ........... B01J 23/8885 (2013.01); B01J 6/004 (2013.01); B01J 8/02 (2013.01); B01J 35/613 (2024.01);
(Continued)

(58) Field of Classification Search
CPC ...... B01J 23/8885; B01J 35/613; B01J 6/004; B01J 8/02; B01J 37/0045; B01J 37/08;
(Continued)

(56) References Cited

U.S. PATENT DOCUMENTS 3,147,084 A     3/1962  Franzen et al.
3,773,692 A  *  11/1973  Hensel ................... B01J 23/687
                                                         502/248

(Continued)

FOREIGN PATENT DOCUMENTS

DE    2201428 A1    7/1973
DE    2513405 A1    10/1976
(Continued)

OTHER PUBLICATIONS

International Search Report and Written Opinion received for PCT Patent Application No. PCT/EP2021/059382, mailed on Jul. 21, 2021, 11 pages (2 pages of English Translation and 9 pages of Original Document).
(Continued)

*Primary Examiner* — Patricia L. Hailey
(74) *Attorney, Agent, or Firm* — Faegre Drinker Biddle & Reath LLP

(57) ABSTRACT

A process for producing a catalytically active multielement oxide comprising the elements Mo, W, V and Cu, wherein at
(Continued)

least one source of the elemental constituents W of the multielement oxide is used to produce an aqueous solution, the resultant aqueous solution is admixed with sources of the elemental constituents Mo and V of the multielement oxide, drying of the resultant aqueous solution produces a powder P, the resultant powder P is optionally used to produce geometric shaped precursor bodies, and the powder P is or the geometric shaped precursor bodies are subjected to thermal treatment to form the catalytically active composition, wherein the aqueous solution used for drying comprises from 1.6% to 5.0% by weight of W and from 7.2% to 26.0% by weight of Mo, based in each case on the total amount of aqueous solution.

15 Claims, 4 Drawing Sheets

(51) Int. Cl.
  B01J 8/02     (2006.01)
  B01J 35/61    (2024.01)
  B01J 37/00    (2006.01)
  B01J 37/08    (2006.01)
  C07C 51/235   (2006.01)

(52) U.S. Cl.
  CPC ........... B01J 37/0045 (2013.01); B01J 37/08 (2013.01); C07C 51/235 (2013.01); *C07C 2523/888* (2013.01)

(58) Field of Classification Search
  CPC .... B01J 35/397; B01J 23/8435; B01J 23/885; B01J 23/8876; B01J 23/8877; C07C 51/235; C07C 2523/888
  USPC ......... 502/321, 311, 312, 318; 562/532, 535
  See application file for complete search history.

(56) References Cited

U.S. PATENT DOCUMENTS

| | | | |
|---|---|---|---|
| 4,093,558 A * | 6/1978 | Grasselli ............... | C07C 51/215 502/215 |
| 4,203,906 A | 5/1980 | Sato et al. | |
| 4,259,211 A * | 3/1981 | Krabetz ................. | B01J 23/34 502/178 |
| 4,892,856 A * | 1/1990 | Kawajiri ............. | B01J 23/8877 502/247 |
| 5,048,601 A | 9/1991 | Yamaguchi et al. | |
| 5,144,091 A | 9/1992 | Martan et al. | |
| 5,739,391 A | 4/1998 | Ruppel et al. | |
| 5,910,608 A * | 6/1999 | Tenten .................... | C07C 45/37 502/319 |
| 5,959,143 A * | 9/1999 | Sugi ........................ | B01J 35/66 562/535 |
| 6,403,829 B1 | 6/2002 | Unverricht et al. | |
| 6,994,833 B1 | 2/2006 | Nishimura et al. | |
| 7,253,308 B1 | 8/2007 | Hechler et al. | |
| 7,524,792 B2 * | 4/2009 | Dieterle ................ | C07C 51/215 502/321 |
| 8,426,335 B2 * | 4/2013 | Yunoki ................. | C07C 51/252 562/533 |
| 2003/0018733 A1 | 1/2003 | Yoon et al. | |
| 2004/0102648 A1 | 5/2004 | Borgmeier et al. | |
| 2008/0269521 A1 | 10/2008 | Hammon et al. | |
| 2010/0152475 A1 | 6/2010 | Raichle et al. | |
| 2011/0275856 A1 | 11/2011 | Karpov et al. | |
| 2019/0262806 A1 | 8/2019 | Tamura et al. | |

FOREIGN PATENT DOCUMENTS

| | | | | |
|---|---|---|---|---|
| DE | 2830765 | A1 | 1/1980 | |
| DE | 2909671 | A1 | 10/1980 | |
| DE | 19910506 | A1 | 9/2000 | |
| DE | 19910508 | A1 | 9/2000 | |
| DE | 19927624 | A1 | 12/2000 | |
| DE | 19948241 | A1 | 4/2001 | |
| DE | 19948523 | A1 | 4/2001 | |
| DE | 19952964 | A1 | 5/2001 | |
| DE | 10051419 | A1 | 4/2002 | |
| DE | 10360057 | A1 | 7/2004 | |
| DE | 10360058 | A1 | 7/2004 | |
| DE | 10350822 | A1 | 6/2005 | |
| DE | 10361456 | A1 | 7/2005 | |
| DE | 102004017150 | A1 | 10/2005 | |
| DE | 60204924 | T2 | 4/2006 | |
| DE | 102007019597 | A1 | 5/2008 | |
| DE | 102008040093 | A1 | 12/2008 | |
| DE | 102008040094 | A1 | 1/2009 | |
| DE | 102008054586 | A1 | 6/2010 | |
| EP | 0383224 | A2 | 8/1990 | |
| EP | 0468290 | A1 | 1/1992 | |
| EP | 0700174 | A1 | 3/1996 | |
| EP | 0700893 | A1 | 3/1996 | |
| EP | 0714700 | A2 | 6/1996 | |
| EP | 0724481 | A1 | 8/1996 | |
| EP | 1138385 | A1 | 10/2001 | |
| EP | 1322585 | A2 | 7/2003 | |
| EP | 1633467 | A1 | 3/2006 | |
| EP | 3056482 | A1 * | 8/2016 | ............ B01J 23/002 |
| EP | 3513874 | A1 | 7/2019 | |
| JP | 58-096041 | A | 6/1983 | |
| JP | 2003210991 | A * | 7/2003 | ............ B01J 27/228 |
| JP | 2007-260588 | A | 10/2007 | |
| JP | 2018-043197 | A | 3/2018 | |
| WO | 95/11081 | A1 | 4/1995 | |
| WO | 02/24620 | A2 | 3/2002 | |
| WO | 2004/085365 | A2 | 10/2004 | |
| WO | 2004/085367 | A1 | 10/2004 | |
| WO | 2004/085368 | A2 | 10/2004 | |
| WO | 2004/085369 | A1 | 10/2004 | |
| WO | 2004/085370 | A1 | 10/2004 | |
| WO | 2004/108267 | A1 | 12/2004 | |
| WO | 2004/108284 | A1 | 12/2004 | |
| WO | 2005/016861 | A1 | 2/2005 | |
| WO | 2005/042459 | A1 | 5/2005 | |
| WO | 2005/047226 | A1 | 5/2005 | |
| WO | 2005/120702 | A1 | 12/2005 | |
| WO | 2006/094766 | A1 | 9/2006 | |
| WO | 2006/114428 | A1 | 11/2006 | |
| WO | 2007/082827 | A1 | 7/2007 | |
| WO | 2008/104577 | A1 | 9/2008 | |
| WO | 2011/134932 | A1 | 11/2011 | |
| WO | WO-2022090019 | A1 * | 5/2022 | ............ B01J 23/002 |

OTHER PUBLICATIONS

International Preliminary Report on Patentability received for PCT Patent Application No. PCT/EP2021/059382, mailed on Nov. 3, 2022, 12 pages (6 pages of English Translation and 6 pages of Original Document).

* cited by examiner

METHOD FOR PRODUCING A CATALYTICALLY ACTIVE MULTI-ELEMENT OXIDE CONTAINING THE ELEMENTS Mo, W, V AND Cu

CROSS-REFERENCE TO RELATED APPLICATIONS

This application is a national stage application (under 35 U.S.C. § 371) of PCT/EP2021/059382, filed Apr. 12, 2021, which claims benefit of European Application No. 20170533.2, filed Apr. 21, 2020, both of which are incorporated herein by reference in their entirety.

DESCRIPTION

The present invention relates to a process for producing a catalytically active multielement oxide comprising the elements Mo, W, V and Cu.

The present invention also relates to the catalytically active multielement oxides obtainable in accordance with the invention, to the use thereof for the catalysis of the heterogeneously catalyzed partial gas phase oxidation of acrolein to acrylic acid and to the use thereof for production of eggshell catalysts particularly suitable for this catalysis, and also to the eggshell catalysts obtainable in accordance with the invention.

Multielement oxides comprising Mo, W, V and Cu are known, for example, from US 2011/0275856, JP 2018-43197, U.S. Pat. No. 6,994,833, EP 1 138 385 A and WO 2004/108267.

US 2011/0275856 and JP 2018-43197 disclose the production of multielement oxides, wherein a source of the elemental constituents W was first used to produce an aqueous solution. Subsequently, sources of the elemental constituents Mo and V of the multielement oxide were added.

U.S. Pat. No. 6,994,833 discloses the preparation of a multielement oxide, wherein sources of the elemental constituents Mo, W and V were used to produce an aqueous solution.

EP 1 138 385 A discloses the preparation of a multielement oxide, wherein sources of the elemental constituents W, V and Mo were used to produce an aqueous solution.

WO 2004/108267 discloses the production of multielement oxides, wherein a source of the elemental constituent Mo was first used to produce an aqueous solution. Subsequently, sources of the elemental constituents V and W of the multielement oxide were added.

A disadvantage of the production of the multielement oxides of US 2011/0275856, of JP 2018-43197, of U.S. Pat. No. 6,994,833, of EP 1 138 385 A and of WO 2004/108267 is the low concentration of Mo, W, V and Cu in the aqueous solution and the associated low space-time yield in the production of the multielement oxide itself.

The object of the present invention was therefore that of providing an improved process for producing a catalytically active multielement oxide comprising the elements Mo, W, V and Cu. The process should especially have improved space-time yield in the production of the catalytically active multielement oxide itself, elevated activity and elevated specific surface area of the catalytically active multielement oxide.

What is accordingly provided is a process for producing a catalytically active multielement oxide comprising the elements Mo, W, V, Cu and optionally Sb, wherein the ratio of the elements conforms to the general formula (I)

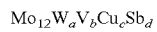

$$Mo_{12}W_aV_bCu_cSb_d \quad (I)$$

where
a=0.4 to 5.0, preferably 0.6 to 3.5, more preferably 0.8 to 2.5, most preferably 1.0 to 2.0,
b=1.0 to 6.0, preferably 1.5 to 5.5, more preferably 2.0 to 5.0, most preferably 2.5 to 4.5,
c=0.2 to 1.8, preferably 0.4 to 1.6, more preferably 0.6 to 1.4, most preferably 0.8 to 1.2, and
d=0.0 to 2.0, preferably 0.1 to 1.6, more preferably 0.2 to 1.2, most preferably 0.3 to 0.8,
and the molar proportion of the element Mo in the total amount of all non-oxygen elements is from 5 to 95 mol %, preferably from 10 to 90 mol %, more preferably from 15 to 85 mol %, most preferably from 20 to 80 mol %, which comprises a) using at least one source of the elemental constituents W of the multielement oxide to produce an aqueous solution or aqueous suspension, b) admixing the aqueous solution or aqueous suspension obtained in a) with sources of the elemental constituents Mo, V and optionally Sb of the multielement oxide, c) admixing the aqueous solution or aqueous suspension obtained in b) with sources of the elemental constituents Cu and optionally Sb of the multielement oxide, d) drying the aqueous solution or aqueous suspension obtained in c) and optionally comminuting to produce a powder P, e) optionally using the powder P obtained in d), optionally with addition of one or more shaping auxiliaries and after homogeneous mixing, to obtain geometric shaped precursor bodies from the resulting mixture, and f) subjecting the powder P obtained in d) or the geometric shaped precursor bodies obtained in e) to thermal treatment to form the catalytically active multielement oxide, wherein the aqueous solution or aqueous suspension used in d) comprises from 1.6% to 5.0% by weight, preferably from 1.9% to 5.2% by weight, more preferably from 2.1% to 4.5% by weight, most preferably from 2.3% to 3.8% by weight, of W and from 7.2% to 26.0% by weight, preferably from 8.7% to 22.0% by weight, more preferably from 10.1% to 18.0% by weight, most preferably from 11.5% to 15.0% by weight, of Mo, based in each case on the total amount of aqueous solution or aqueous suspension.

The stoichiometric coefficient a of the element W in the general formula (I) is preferably 0.6 to 3.5, more preferably 0.8 to 2.5, most preferably 1.0 to 2.0.

The stoichiometric coefficient b of the element V in the general formula (I) is preferably 1.5 to 5.5, more preferably 2.0 to 5.0, most preferably 2.5 to 4.5.

Cu increases selectivity for acrylic acid (there is a drop in $CO_x$ selectivity, i.e. less total combustion), and the activity passes through a maximum.

The stoichiometric coefficient c of the element Cu in the general formula (I) is preferably 0.4 to 1.6, more preferably 0.6 to 1.4, most preferably 0.8 to 1.2.

Sb increases the long-term stability of the catalytically active multielement oxide.

The stoichiometric coefficient d of the element Sb in the general formula (I) is preferably 0.1 to 1.6, more preferably 0.2 to 1.2, most preferably 0.3 to 0.8.

The molar proportion of the element Mo in the total amount of all non-oxygen elements is preferably from 10 to 90 mol %, more preferably from 15 to 85 mol %, most preferably from 20 to 80 mol %.

For production of the catalytically active multielement oxide, in the process of the invention, suitable sources of the elemental constituents Mo, W, V, Cu and optionally Sb are used to produce an aqueous solution or aqueous suspension.

First of all, in a), at least one source of the elemental constituents W is used to produce an aqueous solution or aqueous suspension.

The temperature of the aqueous solution or aqueous suspension in a) is preferably from 60 to 120° C., more preferably from 80 to 110° C., most preferably from 85 to 100° C. The solution or suspension may be preheated, or heated only after the addition of the source of the elemental constituents W. The duration of the addition is not subject to any restrictions. The source of the elemental constituents W is preferably metered in within less than 5 hours, more preferably within 0.1 to 120 minutes, most preferably within 0.2 to 30 minutes. The addition can be effected under standard pressure, reduced pressure or elevated pressure. The pressure is preferably from 0.5 to 2 bar, more preferably from 0.8 to 1.2 bar, most preferably from 0.9 to 1.1 bar. During the dissolving or suspending, the solution is advantageously stirred or pumped in circulation. The time for dissolving or suspending depends on temperature, energy input and concentration, and is preferably not longer than 5 hours, more preferably from 1 to 120 minutes, most preferably from 2 to 60 minutes or 2 to 30 minutes. Preference is given to preparing an aqueous solution in a).

Subsequently, in b), the aqueous solution or aqueous suspension obtained in a) is admixed with sources of the elemental constituents Mo, V and optionally Sb. The sequence of the addition is not subject to any restrictions. Advantageously, in b), the source of the elemental constituents Mo is metered in first. Preference is given to preparing an aqueous solution in b).

In the addition of the sources of the elemental constituents Mo, V and optionally Sb in b), the temperature of the aqueous solution or aqueous suspension should be kept constant. The aqueous solution or aqueous suspension obtained in a) may be cooled or heated prior to the addition. The source of the elemental constituents Mo is preferably metered in within less than 5 hours, more preferably within 0.1 to 120 minutes, most preferably within 0.2 to 45 minutes. The source of the elemental constituents V is preferably metered in within less than 5 hours, more preferably within 0.1 to 120 minutes, most preferably within 0.2 to 30 minutes. The optional source of the elemental constituents Sb is preferably metered in within less than 5 hours, more preferably within 0.1 to 120 minutes, most preferably within 0.2 to 20 minutes. The addition can be effected under standard pressure, reduced pressure or elevated pressure. The pressure is preferably from 0.5 to 2 bar, more preferably from 0.8 to 1.2 bar, most preferably from 0.9 to 1.1 bar. During the dissolving or suspending, the solution or suspension is advantageously stirred or pumped in circulation. The time for dissolving or suspending depends on temperature, energy input and concentration, and is preferably not longer than 5 hours, more preferably from 1 to 120 minutes, most preferably from 2 to 60 minutes or 2 to 30 minutes.

The pH is preferably from 3 to 8, more preferably from 4 to 7, most preferably from 5 to 7.

Ammonium paratungstate heptahydrate is the preferred source for the elemental constituent W. Ammonium heptamolybdate tetrahydrate is the preferred source for the elemental constituent Mo. Ammonium metavanadate is the preferred source for the elemental constituent V. Antimony acetate or antimony oxide are the preferred sources for the elemental constituent Sb.

Other useful sources for the elemental constituents aside from oxides are quite generally, in particular, metalates, polymetalates, halides, nitrates, formates, oxalates, acetates, carbonates and hydroxides.

If the solubility of a source of a possible elemental constituent in aqueous medium is intrinsically inadequate for the purposes of the process of the invention, it is possible, for example, to suitably modify the pH of the aqueous medium by addition of appropriate modifiers, in order to improve the solubility of the source of an elemental constituent in the aqueous medium. Suitable modifiers include particularly those Brønsted acids and Brønsted bases which decompose to gaseous constituents under the action of elevated temperatures, as employed in the thermal treatment of the geometric shaped precursor bodies to form the desired catalytically active multielement oxide. Examples of such pH modifiers include ammonia, nitric acid, hydrochloric acid, acetic acid, formic acid, oxalic acid and ammonium salts of strong and weak Brønsted acids, such as ammonium nitrate, ammonium chloride, ammonium carbonate, ammonium hydrogen-carbonate, ammonium acetate, ammonium formate and ammonium oxalate.

Alternatively and/or additionally, complexing agents soluble in the aqueous medium can also be added thereto, these decomposing to gaseous compounds and/or escaping as gaseous compounds under the action of elevated temperatures, at least in the presence of molecular oxygen, and being able to complex elemental constituents that are in ionic form in the sources, which generally likewise leads to an improvement in solubility in the aqueous medium. Examples of such complexing agents include ammonia and ethylenediaminetetraacetic acid and salts thereof, preferably those of good water solubility.

A further measure for improving solubility in an aqueous medium is the employment of elevated temperatures. It is of course also possible, in the context of the inventive procedure, to simultaneously employ more than one of the various options addressed for improving solubility in an aqueous medium.

Surprisingly, the solubility of the at least one source of the elemental constituents W depends on the sequence of metered addition. The source of the elemental constituents W has to be metered in before the sources of the elemental constituents Mo, V and optionally Sb. In the case of the incorrect sequence of metered addition, the source of the elemental constituents W is dissolved only incompletely.

Thereafter, in c), the aqueous solution or aqueous suspension obtained in b) is admixed with sources of the elemental constituents Cu and optionally Sb. The source for the elemental constituent Cu is advantageously added here in solid form.

In the addition of the at least one source of the elemental constituents Cu in c), the temperature of the aqueous solution or aqueous suspension should be kept constant. The aqueous solution or aqueous suspension obtained in b) may be cooled or heated prior to the addition. The source of the elemental constituents Cu is preferably metered in within less than 5 hours, more preferably within 0.1 to 120 minutes, most preferably within 0.2 to 20 minutes. The addition can be effected under standard pressure, reduced pressure or elevated pressure. The pressure is preferably from 0.5 to 2 bar, more preferably from 0.8 to 1.2 bar, most preferably from 0.9 to 1.1 bar. During the dissolving or suspending, the solution or suspension is advantageously stirred or pumped in circulation. The time for dissolving or suspending depends on temperature, energy input and concentration, and is preferably not longer than 5 hours, more preferably from 1 to 120 minutes, most preferably from 2 to 60 minutes or 2 to 30 minutes.

The pH is preferably from 3 to 8, more preferably from 4 to 7, most preferably from 5 to 7.

Useful sources for the elemental constituent Cu for the production of multielement oxides according to the invention especially include copper(II) sulfate pentahydrate, copper(II) nitrate hydrate (Cu content=26.1% by weight) and copper(II) acetate monohydrate, among which the latter is preferred. Antimony acetate or antimony oxide are the preferred sources for the elemental constituent Sb.

As well as the sources of the elemental constituents Mo, W, V, Cu and optionally Sb, it is possible to add further sources of elemental constituents in the process of the invention, for example Ta, Cr, Ce, Ni, Co, Fe, Mn, Zn, Nb, Bi, Li, Na, K, Rb, Cs, Mg, Ca, Sr, Ba, Si, Al, Ti and Zr.

In d), the aqueous solution or aqueous suspension obtained in c) is dried and optionally comminuted to produce a powder P.

The aqueous solution or aqueous suspension used for drying d) preferably comprises from 1.9% to 5.2% by weight, more preferably from 2.1% to 4.5% by weight, most preferably from 2.3% to 3.8% by weight, of W, based in each case on the total amount of aqueous solution or aqueous suspension.

The aqueous solution or aqueous suspension used for drying d) preferably comprises from 8.7% to 22.0% by weight, more preferably from 10.1% to 18.0% by weight, most preferably from 11.5% to 15.0% by weight, of Mo, based in each case on the total amount of aqueous solution or aqueous suspension.

By spray-drying the aqueous solution or aqueous suspension obtained in c), it is possible to produce a powder P directly.

In the spray-drying operation, the aqueous solution or aqueous suspension is appropriately introduced by means of a nozzle which can be operated by liquid pressure, compressed air or inert gas, or by means of rotating atomizer disks, divided into fine droplets into a hot gas stream, preferably into a hot air stream, which dries it within fractions of a second to give the powder P. The hot gas stream may in principle flow in the direction counter to the spray jet, i.e. in counter-current, or preferably with the spray jet, i.e. in cocurrent. The spray tower may be operated with a gas stream preheated directly or indirectly. Preference is given to using a directly heated gas stream in which hot fuel gas generated, for instance, by combustion of a fuel, for example methane, is mixed with an additional air stream, for example, and run to the spray tower. Typical inlet temperatures for the hot gas stream are in the range from 250 to 390° C., preferably in the range from 270 to 380° C., and typical outlet temperatures are in the range from 90 to 150° C. The residual water content of the resulting powder P, based on the total mass thereof, is appropriately not more than 10% by weight and particularly appropriately not more than 6% by weight. Low residual water contents are advantageous. In general, the aforementioned residual water content is typically at least 0.5% by weight, frequently at least 2% by weight. Analyses for residual water contents in this document are based generally on the determination thereof with the aid of the HB43 Moisture Analyser from Mettler Toledo AG Laboratory & Weighing Technologies in CH-8606 Greifensee. For this purpose, about 5 g of catalyst is heated to 120° C. by means of infrared radiation within about 50 seconds and kept at that temperature. The measurement is ended when the weight loss within 20 seconds is less than 1 mg.

In general, powders P obtainable as described have comparatively homogeneous particle diameters.

On the way from the site of production thereof to the spray drying apparatus, the aqueous solution or aqueous suspension to be spray dried is advantageously passed through at least one filter, in order to remove any coarse particles present therein, which could, for example, block the spray nozzles, prior to the entry thereof into the spray drying apparatus. The temperature of the conveying conduit here is appropriately kept at the final value of the production temperature of the aqueous solution or of the aqueous suspension. The residual solution or residual suspension which is yet to be spray dried in each case is advantageously mixed constantly by stirring and kept at the starting temperature relevant for the spray drying thereof.

In industry, the aqueous solution or aqueous suspension to be spray dried is normally produced in stirred vessels manufactured from stainless steel of the 1.4541 type (DIN EN 10020). The spray drying apparatus and the stirrer are appropriately manufactured from the same material.

The powder P obtained in d) can be subjected to direct thermal treatment (also referred to as calcining) in f) to form the catalytically active multielement oxide. It is alternatively possible first to produce geometric shaped precursor bodies in e).

The geometric shaped precursor bodies to be subjected to thermal treatment in the process of the invention may be produced from the powder P in the individual case by using different process variants.

In a simple embodiment of the process of the invention, the powder P is used to directly form geometric shaped precursor bodies of any desired geometry by compaction, such as press agglomeration or tableting (as indicated by way of example, for example, in documents DE 10 2008 054586 A, DE 10 2008 040093 A and DE 10 2008 040094 A for comparable pulverulent mixtures). Examples of shaped precursor body geometries typical in accordance with the invention are spheres (the diameter of which may, for example, be from 2 to 10 mm), and also solid cylinders or hollow cylinders (rings) having an external diameter and a length of typically from 2 to 10 mm. In the case of the hollow cylinder, a wall thickness of 1 to 3 mm is appropriate.

It is of course possible to additionally mix auxiliaries for subsequent shaping (shaping auxiliaries) into the powder P. Useful auxiliaries include glidants or lubricants such as graphite, carbon black, polyethylene glycol, stearic acid, salts of stearic acid, starch, polyacrylic acid, mineral oil, vegetable oil, water, boron nitride, boron trifluoride, glycerol, fine Teflon powder and/or cellulose ether.

The aforementioned lubricants may partly or fully decompose and/or be chemically converted in the course of the thermal treatment of the geometric shaped precursor bodies, possibly to form substances which escape in gaseous form.

As further shaping assistants, the mixture to be compacted may comprise added reinforcing agents, which promote coherence in the resulting geometric shaped precursor bodies. Such reinforcing agents may, for example, be microfibers of glass, asbestos, silicon carbide and/or potassium titanate.

In contrast to the lubricants, reinforcing assistants are normally essentially preserved in the course of the inventive thermal treatment of the geometric shaped precursor bodies.

It is of course also possible to additionally mix in lubricants and reinforcing agents together.

Based on the total amount of a pulverulent mixture to be compacted in accordance with the invention to shaped precursor bodies, the total amount of shaping assistants present will generally not be more than 30% by weight, usually not more than 20% by weight and in many cases not more than 10% by weight (but frequently at least 0.1% by weight, or at least 0.2% by weight, or at least 0.5% by weight, or at least 1% by weight).

If the shaping in the production of the geometric shaped precursor bodies is effected by extrusion or strand pressing, it is advantageous to additionally mix in at least one liquid (a liquid binder). This liquid is preferably water, an aqueous solution and/or constituents of an aqueous solution. Advantageously, at least one aforementioned liquid shaping assistant incorporated is a lower ($C_2$ to $C_5$) organic carboxylic acid (e.g. formic acid, acetic acid (preferred), propionic acid, fumaric acid and/or maleic acid or the respective aqueous solution thereof and/or the constituents of such an aqueous solution).

Calculated as pure lower organic carboxylic acids, these (preferably acetic acid) are advantageously incorporated overall in a total amount of 5 to 15% by weight, based on the content of powder P in the overall mixture. The total water content of the resulting overall mixture may be from 5% to 45% by weight, preferably from 10% to 30% by weight.

The incorporation of one or more lower organic carboxylic acids (preferably acetic acid) and/or the aqueous solution thereof is appropriately effected by kneading with maximum homogeneity. The temperature in the course of kneading will generally not be more than 50° C. Typically, the aforementioned temperature is in the range from 20 to 50° C., appropriately in the range from 30 to 40° C. The kneading takes preferably less than 12 hours, more preferably from 10 to 360 minutes, most preferably from 20 to 120 minutes.

The resulting plastically formable mass (the resulting kneading material, the resulting kneading composition) is subsequently shaped by extrusion to shaped bodies (shaped precursor bodies) of the desired geometry. In the simplest case, these may be strands (solid cylinders). Of course, rings are also possible extrudates in accordance with the invention.

In the case of geometric shaped precursor bodies obtained by extrusion, a thermal treatment thereof includes the drying thereof. In general, this drying is effected at temperatures of less than 200° C., preferably of not more than 150° C., but typically at temperatures of at least 60° C., or at least 80° C., or at least 100° C.

Subsequently, the powder P obtained in d) or the shaped precursor bodies obtained in e) are subjected to thermal treatment to form the catalytically active multielement oxide (also referred to as calcination).

The calcination is conducted at end temperatures of 200 to 600° C., preferably of 300 to 500° C., more preferably of 370 to 430° C. (material temperature in each case). Especially during the calcination, the material, advantageously in accordance with the invention, has a very substantially uniform temperature.

The calcination can be performed batchwise or continuously.

In the case of batchwise calcination, it is possible to employ temperature programs with one or more temperature plateaus, as described in EP 1 633 467 A. The heating rate is preferably from 0.1 to 20 K/min, more preferably from 0.5 to 10 K/min, most preferably from 1 to 5 K/min.

In the case of continuous calcination, the material migrates through an oven. The calcination may be conducted here isothermally or using different temperature zones, as described in EP 1 322 585 A. The temperature of the first temperature zone is preferably at least 30° C. lower than the highest temperature of the other temperature zones.

The calcination may be conducted in a stationary or moving bed of the powder P or of the shaped precursor bodies. The calcination of the shaped precursor bodies is preferably conducted in a moving bed. Suitable apparatuses are rotary furnaces as described in EP 1 633 467 A, or belt calciners as described in EP 1 322 585 A. Rotary furnaces are preferred.

The thermal treatment (especially the calcination) of the powder P or of the geometric shaped precursor bodies can be performed either under inert gas or under an oxidative (gas) atmosphere, for example air (or another mixture of inert gas and oxygen), or else under a reducing atmosphere (for example mixtures of inert gas and reducing gases such as hydrogen, ammonia, carbon monoxide, methane and/or acrolein or said reducing gases alone) (it will be appreciated that an atmosphere having reducing action overall may also have a limited content of molecular oxygen). The oxidative (gas) atmosphere preferably comprises from 1% to 15% by volume, more preferably from 1.5% to 10% by volume, most preferably from 2% to 8% by volume, of molecular oxygen. The preferred oxidative (gas) atmospheres comprise, as well as molecular oxygen, inert gases such as nitrogen, and water vapor. The water vapor content is preferably less than 5% by volume, more preferably less than 2% by volume. Oxygen contents above and below the aforementioned limits normally reduce the resulting catalytic activity. The thermal treatment can in principle alternatively be effected under reduced pressure.

In the calcination, there can be uncontrolled generation of heat in the powder P or in the shaped precursor body, resulting in damage to the catalytically active multielement oxide to be produced. When ammonium salts are used, for example at temperatures of 150 to 350° C., ammonia is released during the calcination and can burn. The uncontrolled generation of heat can be limited by sufficient exchange of heat and gas. It is alternatively possible to adjust the amount of material to be calcined, the amount and the composition of the atmosphere, and the temperature program.

If the thermal treatment of the powder P or of the geometric shaped precursor bodies is effected under gaseous atmosphere, this may either be stationary or may flow.

Overall, the thermal treatment (especially the calcination) of the powder P or of the geometric shaped precursor bodies may take up to 24 hours or more. Frequently, the thermal treatment (especially the calcination) extends over a period of minutes up to a few hours, for example from 0.5 to 10 hours, or from 1 to 5 hours. Elevated temperatures are normally associated with shorter durations of the thermal treatment (especially of the calcination) and, at lower temperatures, generally longer periods of thermal treatment (especially of the calcination) are employed. High temperatures and long treatment times (especially of the calcination) generally reduce the specific surface area of the catalytically active multielement oxides which result in the course of thermal treatment of the geometric shaped precursor bodies (of the precursor composition).

The specific BET surface area of the catalytically active multielement oxides obtained in accordance with the invention is typically from 16 to 35 $m^2/g$, preferably from 17 to 32 $m^2/g$, more preferably from 18 to 29 $m^2/g$, most preferably from 19 to 26 $m^2/g$ (determined by gas adsorption ($N_2$) according to Brunauer-Emmett-Teller (BET)). A description of the BET determination method can be found in DIN ISO 9277 and in J. Am. Chem. Soc. Vol. 60, No. 2, pages 309-319 (1938).

The thermal treatment (especially the calcination) of the geometric shaped precursor bodies is preferably effected in a gas atmosphere comprising oxygen and ammonia. The ammonia may evolve from the shaped precursor bodies themselves by virtue of an appropriate amount of ammonium ions being incorporated into it.

The resulting catalytic activity of the catalytically active multielement oxide obtained in the thermal treatment generally exhibits an optimum depending on the oxygen content of the calcination atmosphere.

Calcination processes suitable in accordance with the invention are disclosed, for example, by documents WO 2004/108284, EP 0 724 481 A, WO 2008/104577, WO 2004/108267 and WO 95/11081, among which the calcination process disclosed in the latter WO document is especially preferred.

The geometric shaped catalyst bodies which are obtained (are the result) within a thermal treatment of geometric shaped precursor bodies can be used as such (as what are called unsupported catalysts) in the fixed catalyst bed for catalysis of the heterogeneously catalyzed partial gas phase oxidation of acrolein to acrylic acid.

Unsupported catalyst geometries suitable in accordance with the invention are, for example, solid cylinders or hollow cylinders having an external diameter and a length of 2 to 10 mm. In the case of the hollow cylinders, a wall thickness of 1 to 3 mm is appropriate. The unsupported catalyst may of course also have spherical geometry, in which case the sphere diameter may be from 2 to 10 mm.

It is also possible for the geometric shaped catalyst bodies obtainable by the process according to the invention (the catalytically active multielement oxides obtainable in accordance with the invention; the catalyst obtainable in accordance with the invention), especially when they have been obtained in a not particularly homogeneous geometry, to be converted to a finely divided form (for example comminuted to powder or spall) and used for catalysis of a heterogeneously catalyzed partial oxidation of acrolein to acrylic acid (including in a fluidized or moving bed).

Particularly advantageously in accordance with the invention, the catalytically active multielement oxides will, however, be converted to a finely divided form (for example comminuted to powder or spall, for example by grinding), and this finely divided form will be applied as a shell of the catalytically active multielement oxide to the outer surface of a geometric shaped support body (to obtain what is called an eggshell catalyst).

Typically, the application is effected with the aid of a liquid binder. It functions as a bonding fluid, with the aid of which the finely divided catalytically active multielement oxide is bonded to the outer surface of the geometric shaped support body. Subsequently, the bonding fluid is at least partly removed again from the coated geometric shaped support body (for example by passing over hot gas, as described in WO 2006/094766). The residual water content of the resulting catalyst is preferably not more than 1.0% by weight, more preferably not more than 0.5% by weight, most preferably not more than 0.2% by weight, based in each case on the total mass of the catalyst.

Useful materials for the geometric shaped support bodies especially include aluminas, silicas, silicates such as clay, kaolin, steatite (preferably C-220 steatite from Ceram Tec (DE), or preferably with a low water-soluble alkali content), pumice, aluminum silicate, magnesium silicate, silicon carbide and zirconia. The geometric shaped support bodies are appropriately substantially inert with respect to the relevant partial oxidation (i.e., when they are used alone as "catalysts" for the corresponding heterogeneously catalyzed partial gas phase oxidation of, for example, acrolein to acrylic acid, they are largely inert, meaning that they cause essentially no conversion of the acrolein).

The outer surface of the geometric shaped support body may be either smooth or rough. Advantageously, the outer surface of the geometric shaped support body is rough, since increased surface roughness generally causes increased bond strength of the catalytically active multielement oxides applied.

Useful geometric shaped support bodies having distinct surface roughness include especially shaped support bodies having a grit layer on their outer surface (geometric shaped support bodies preferred in accordance with the invention are hollow cylinders with a grit layer on their outer surface).

The surface roughness $R_z$ of the outer surface of the geometric shaped support body is preferably in the range from 30 to 100 μm, more preferably in the range from 50 to 70 μm (determined to DIN 4768 Sheet 1 with a "Hommel Tester for DIN-ISO surface measurement parameters" from Hommelwerke). Particular preference is given to roughsurface geometric shaped support bodies from Ceram Tec (DE) made of C220 steatite.

The support materials may be porous or nonporous. The support material is preferably nonporous (the total volume of the pores of the geometric shaped support body is, based on the volume of the respective geometric shaped support bodies, advantageously not more than 1% by volume). The specific (based on the unit of its mass) BET surface area of the support material is accordingly preferably low.

The geometric shaped support bodies may be of regular or irregular shape, preference being given to regularly shaped geometric shaped support bodies.

The longest extent of the geometric shaped support bodies is normally in the range from 1 to 10 mm (the longest extent is the longest direct line connecting two points on the outer surface of a shaped support body).

Preference is given to employing spheres or (solid) cylinders, especially hollow cylinders (rings) or Berl saddles, as geometric shaped support bodies. Favorable diameters for support spheres are from 1 to 6 mm. If cylinders are used as geometric shaped support bodies, the length thereof is preferably from 2 to 10 mm and the external diameter thereof preferably from 4 to 10 mm. In the case of rings, the wall thickness is additionally typically from 1 to 4 mm. Hollow cylindrical geometric shaped support bodies of length 3 to 8 mm, external diameter 4 to 8 mm and wall thickness 1 to 2 mm are very particularly preferred geometric shaped support bodies. Examples of favorable ring geometries for shaped support bodies include hollow cylinders of geometry 7 mm×3 mm×4 mm (external diameter× length×internal diameter) and of geometries 6 mm×6 mm×4 mm, 7 mm×7 mm×5 mm and 5 mm×3 mm×2 mm. Favorable geometric shaped support bodies are also all shaped support bodies disclosed in Research Disclosure Database Number 532036 in August 2008 (especially all those disclosed therein by way of example). The production of eggshell catalysts CE and IE disclosed in the present document can also be performed with any annular shaped support body disclosed by way of example therein (especially with those of geometry 7 mm×4 mm×3 mm or 6 mm×6 mm×4 mm).

The thickness of the shell of catalytically active multielement oxide applied to the outer surface of the geometric shaped support bodies (especially of the above-detailed annular shaped support bodies, the outer surface of which also includes the surface delineating the cavity of the ring) is appropriately and generally 10 to 1000 μm. This shell thickness in the case of eggshell catalysts is preferably from 10 to 500 μm, more preferably from 100 to 500 μm and most preferably from 200 to 450 μm.

FIG. 3 shows an x-ray microtomography (X-ray μCT) of an annular eggshell catalyst. FIG. 4 and FIG. 5 show x-ray diffractions of annular eggshell catalysts. The eggshell catalysts were coated annular support bodies (external diameter 7 mm, length 3 mm, internal diameter 4 mm, surface roughness Rz 45 μm) of the steatite C 220 type (Ceram Tec GmbH, Plochingen, Germany) and had an oxidic active composition content of about 20% by weight.

Advantageously, the shell thickness is very substantially homogeneous over an individual eggshell catalyst. In the case of production of a relatively large production batch of eggshell catalysts, the shell thickness is likewise very substantially homogeneous over several individual eggshell catalyst ring bodies. The aforementioned homogeneity of the shell thickness is appropriately frequently within the range of those figures which have been given in the working examples of DE 103 60 058 A.

The finely divided catalytically active multielement oxide can be applied to the outer surface of the geometric shaped support body, for example, by first moistening the outer surface with the liquid binder in a controlled manner (for example by spraying). By contacting the geometric shaped support body thus moistened with the finely divided catalytically active multielement oxide, a layer of the active composition is subsequently fixed on the moistened surface (for example, dust the moistened geometric shaped support bodies as described in EP 0 714 700 A with the finely divided catalytically active multielement oxide (with the active composition powder)).

In this context, "moisten in a controlled manner" means that the support surface is appropriately moistened in such a way that it does have absorbed liquid binder, but no liquid phase as such is visually apparent on the support surface. If the support surface is too moist, the finely divided catalytically active multielement oxide agglomerates to give separate agglomerates, rather than adhering to the surface. Details of this can be found in DE 29 09 671 A and in DE 100 51 419 A, and also in EP 0 714 700 A. It will be appreciated that the operation can be repeated periodically to achieve an increased layer thickness. In this case, the coated base body becomes the new "support body", etc.

It is alternatively possible to employ all other application processes acknowledged as prior art in EP 0 714 700 A for production of the above-detailed eggshell catalysts.

Examples of useful liquid binders include water, an organic solvent or a solution of an organic substance (for example of an organic solvent) in water, or in an organic solvent, or in an aqueous solution of an organic solvent. Examples of organic binders include mono- or polyhydric organic alcohols, such as ethylene glycol, 1,4-butanediol, 1,6-hexanediol or glycerol, mono- or polybasic organic carboxylic acids such as propionic acid, oxalic acid, malonic acid, glutaric acid or maleic acid, amino alcohols such as ethanolamine or diethanolamine, and mono- or polyfunctional organic amides such as formamide. Suitable organic binder constituents (binder promoters) soluble in water, in an organic liquid or in a mixture of water and an organic liquid are monosaccharides and oligosaccharides such as glucose, fructose, sucrose and/or lactose.

Particularly advantageously, the liquid binder used is a solution consisting of 20% to 90% by weight of water and 10% to 80% by weight of an organic compound. The organic component in the aforementioned liquid binders is preferably 10% to 50% by weight and more preferably 20% to 30% by weight. Very particularly preferred liquid binders are solutions which consist of 20% to 90% by weight of water and 10% to 80% by weight of glycerol. Advantageously, the glycerol content in these aqueous solutions is 10% to 50% by weight and more preferably 20% to 30% by weight. One reason for the advantage of preferred binders is that they are able to fully satisfactorily wet both the finely divided catalytically active multielement oxide (or the finely divided precursor composition (see below)) and the outer surface of the geometric shaped support bodies.

The fineness of the finely divided catalytically active multielement oxide (or the precursor composition thereof (see below)) to be applied on the outer surface of the geometric shaped support body will of course be matched to the desired shell thickness. For the shell thickness range from 100 to 500 μm, suitable active composition powders are those of which at least 50% of the total number of the preferably granular powder particles pass through a sieve of mesh size (circular meshes) 1 to 20 μm or alternatively 1 to 10 μm, and wherein the numerical proportion of particles having a longest dimension above 50 μm (of particles which do not pass through a sieve of mesh size (circular meshes) 50 μm) is less than 10% by weight. For the rest, the statements made on page 18 of WO 2005/120702 are correspondingly applicable.

Eggshell catalysts obtainable as described will preferably be obtained by the mode of production described and detailed by way of example in EP 0 714 700 A (see also WO 2011/134932 and the working examples of DE 103 60 057 A). An aqueous solution of 75% by weight of water and 25% by weight of glycerol is the preferred liquid binder. The process for thermal treatment of the geometric shaped precursor bodies will, advantageously in accordance with the invention, be performed according to the procedure described and detailed by way of example in DE 103 60 057 A.

The procedure of the invention alternatively encompasses those processes for producing a catalytically active multielement oxide in which the shaping of geometric shaped precursor bodies with the (finely divided) mixture consisting of a powder P and optionally one or more shaping aids is effected in such a way that (in a manner corresponding to that described for the application of an active composition shell) a shell of this (finely divided) mixture (of the finely divided precursor composition) is applied directly as such to the outer surface of a geometric shaped support body. In the course of the thermal treatment of the geometric shaped precursor bodies thus obtained (which also comprises the at least partial removal of the liquid binder additionally used for the application), eggshell catalysts of the invention in which a shell of catalytically active multielement oxide has been applied on the outer surface of a (catalytically essentially inert) geometric shaped support body are obtained directly.

As already mentioned, catalytically active multielement oxides obtainable in accordance with the invention are especially suitable for catalysis of a heterogeneously catalyzed partial gas phase oxidation of acrolein to acrylic acid, as described in WO 2007/082827, WO 2004/085365, WO 2004/085367, WO 2004/085368, WO 2004/085369, WO 2004/085370, WO 2005/016861, WO 2005/047226 and WO 2005/042459. They are notable especially in that a catalyst bed charged therewith, in the course of performance of the partial oxidation, has a long service life during which the target product is formed with high activity. The preferred use form of a catalytically active multielement oxide obtainable in accordance with the invention is that of an eggshell catalyst that preferably has an annular geometry. Particular preference is given here to using the eggshell catalyst detailed by way of example in the example of the present document, for example in all working examples and in all comparative examples of the above WO documents WO 2007/082827, WO 2004/085365, WO 2004/085367, WO 2004/085368, WO 2004/085369, WO 2004/085370, WO 2005/016861, WO 2005/047226 and WO 2005/042459, in each of which it is capable of replacing the catalyst used therein (the statements made therein for the eggshell catalyst from the example of the present document are also applicable to the eggshell catalyst from the comparative example of the present document).

In principle, catalytically active multielement oxides obtainable in accordance with the invention are also suitable in a correspondingly advantageous manner for catalysis of the heterogeneously catalyzed partial gas phase oxidation of methacrolein to methacrylic acid.

The above is particularly true when the heterogeneously catalyzed partial gas phase oxidation of acrolein or methacrolein (i.e., in abbreviated form, of "(meth)acrolein") to acrylic acid or methacrylic acid (i.e., in abbreviated form, to "(meth)acrylic acid") is performed at high (meth)acrolein loads, as described in DE 103 07 983 A, DE 199 48 523 A, DE 199 10 508 A, WO 2008/104577, WO 2011/134932, DE 199 27 624 A and DE 103 60 057 A.

The heterogeneously catalyzed partial gas phase oxidation can be performed in a manner known per se. In other words, a reaction gas mixture comprising the (meth)acrolein, molecular oxygen and at least one inert diluent gas is conducted at elevated temperature through a catalyst bed, the catalysts of which comprise, as the active composition, at least one catalytically active multielement oxide obtainable in accordance with the invention, and the conversion thereof to (meth)acrylic acid is effected during the residence time of the (meth)acrolein in the catalyst bed. The catalyst bed is preferably a fixed catalyst bed. In principle, however, a fluidized bed or a moving bed is also useful for the process according to the invention. In general, steam as a constituent of the reaction gas mixture leads to an improvement in selectivity and activity. In addition, inert diluent gases having elevated molar specific heat, such as n-propane or carbon dioxide, are advantageous. These are gases that undergo chemical change as the reaction gas mixture passes through the catalyst bed preferably to an extent of not more than 5 mol %, more preferably to an extent of not more than 3 mol %, most preferably to an extent of not more than 1 mol %, or not at all.

For performance of the gas phase partial oxidation of (meth)acrolein, heat exchanger reactors in particular are suitable. A heat exchanger reactor has at least one primary space and at least one secondary space, which are separated from one another by a dividing wall. In the at least one primary space is positioned the catalyst charge which comprises at least one catalytically active multielement oxide which is obtainable in accordance with the invention and through which a reaction gas mixture comprising (meth) acrolein flows. At the same time, a fluid heat carrier flows through the secondary space and heat exchange takes place between the two spaces through the dividing wall, the purpose of which is to monitor and to control the temperature of the reaction gas mixture on its way through the catalyst bed.

In general, the gas phase partial oxidation of the (meth) acrolein is performed in a shell-and-tube (heat exchanger) reactor having one or more temperature zones, as described in EP 0 700 174 A, EP 0 700 893 A, DE 199 10 508 A, DE 199 48 523 A, DE 199 10 506 A, DE 199 48 241 A, DE 28 30 765 A, DE 25 13 405 A, U.S. Pat. No. 3,147,084, DE 22 01 428 A, EP 0 383 224 A, JP 2007-260588 and JP S58-096041.

A fixed catalyst bed here takes the form of a corresponding bed of shaped catalyst bodies (optionally in a mixture with diluting inert geometric shaped bodies) in the metal tubes (catalyst tubes) of the shell-and-tube reactor, and the temperature medium is, or the temperature media are, conducted around the metal tubes (in the case of more than one temperature zone, a corresponding number of spatially essentially separate temperature media are conducted around the metal tubes). The temperature medium is generally a salt melt. The reaction gas mixture is conducted through the catalyst tubes.

Alternatively, the fixed catalyst bed may also be within the spaces between thermoplates, through which a heat carrier flows, in a thermoplate reactor, as recommended in DE 10 2004 017 150 A, DE 199 52 964 A and DE 103 61 456 A.

The fixed catalyst bed may, as already stated, quite generally consist only of catalysts obtainable in accordance with the invention, but also of such catalysts diluted with inert geometric shaped bodies. The inert geometric shaped bodies here may be the geometric shaped support bodies (support bodies) used for production of inventive eggshell catalysts. Upstream of and/or beyond the fixed bed catalyst may be disposed a bed purely of inert shaped bodies (such beds purely of inert shaped bodies are not normally included in the calculation of the space velocity of reaction gas or of a reaction gas component on the fixed catalyst bed).

Catalyst tubes used in a shell-and-tube reactor are customarily manufactured from ferritic steel and typically have a wall thickness of 1 to 3 mm. Their internal diameter is generally from 20 to 30 mm, frequently from 21 to 29 mm or from 21 to 26 mm. Their length is appropriately from 2 to 4 m.

The number of catalyst tubes accommodated in the shell-and-tube vessel appropriately runs to at least 5000, preferably to at least 10 000. Frequently, the number of catalyst tubes accommodated in the reactor vessel is 15 000 to 40 000. Shell-and-tube reactors having a number of catalyst tubes exceeding 50 000 are usually exceptional. Within the vessel, the catalyst tubes are normally arranged in homogeneous distribution (preferably 6 equidistant neighboring tubes per catalyst tube), the distribution appropriately being selected such that the separation of the central internal axes of mutually adjacent catalyst tubes (called the catalyst tube pitch) is 35 to 45 mm (cf., for example, EP 0 468 290 A).

A particularly favorable heat exchange medium for shell-and-tube reactors is the use of melts of salts such as potassium nitrate, potassium nitrite, sodium nitrite and/or sodium nitrate, or of low-melting metals such as sodium, mercury and alloys of different metals.

Charging of catalyst tubes in shell-and-tube reactors with catalysts obtainable in accordance with the invention (especially those detailed in the example (but also in the comparative example) of the present document) is advantageous particularly when the shell-and-tube reactor is operated at a (meth)acrolein space velocity on the catalyst charge of at least 130 l (STP)/l·h, or at least 150 l (STP)/l·h, or at least 160 l (STP)/l·h, or at least 170 l (STP)/l·h, or at least 180 l (STP)/l·h, or at least 200 l (STP)/l·h, or at least 220 l (STP)/l·h, or at least 240 l (STP)/l·h, or at least 260 l (STP)/l·h. Of course, such a catalyst charge is also advantageous in the case of smaller (for example not more than 130 l (STP)/l·h, or not more than 100 l (STP)/l·h, or not more than 80 l (STP)/l·h, or not more than 60 l (STP)/l·h) (meth)acrolein space velocities.

In general, the (meth)acrolein space velocity on the catalyst charge will be at least 400 l (STP)/l·h, or at least 350 l (STP)/l·h, or at least 300 l (STP)/l·h, or at least 280 l (STP)/l·h (corresponding space velocities can also be implemented in thermoplate reactors).

The space velocity of reaction gas input mixture on a fixed catalyst bed is understood in this document to mean the amount of reaction gas input mixture in standard liters (=l (STP); the volume in liters that the corresponding gas volume would occupy under standard conditions, i.e. at 0° C. and 101.3 kPa)) which is supplied to the fixed catalyst bed, based on the volume of the bed thereof (bed sections composed purely of inert material are not included in the volume of the bed; incidentally, the volume of a bed is the volume of the empty space occupied by the bed (or by the relevant sections thereof)), i.e. based on the bed volume thereof, per hour (→unit=l (STP)/l·h).

The space velocity may also be based only on one constituent of the reaction gas input mixture (for example only on the organic starting compound to be partially oxidized). In that case, it is correspondingly the volume of this constituent (for example of the organic starting compound of the partial oxidation) in standard liters which is supplied to the fixed catalyst bed, based on the volume of the bed thereof (bed sections composed purely of inert material are not included in the volume of the bed; incidentally, the volume of a bed is the volume of the empty space occupied by the bed (or by the relevant sections thereof)), per hour (→unit=l (STP)/l·h).

The volume-specific activity of the fixed catalyst bed will generally be configured such that it increases in flow direction of the reaction gas.

This can be achieved in a simple manner by decreasing the level of dilution of the fixed catalyst bed with inert shaped bodies in flow direction of the reaction gas. The volume-specific activity can alternatively be adjusted by using catalysts having different specific BET surface area. It is additionally possible to use eggshell catalysts having different pore volume or different eggshell thickness. Activity increases here with increasing specific BET surface area, pore volume or eggshell thickness.

Otherwise, the heterogeneously catalyzed partial oxidation with eggshell catalysts obtainable in accordance with the invention can quite generally be performed in all aspects as detailed by DE 103 50 822 A. The (meth)acrolein content in the reaction gas input mixture may have values of 3% to 15% by volume, frequently of 4% to 10% by volume, or of 5% to 8% by volume (based in each case on the total volume of the reaction gas input mixture).

The molar ratio of oxygen to (meth)acrolein in the reaction gas input mixture will normally be at least 1. Typically, this ratio will have values of not more than 3. In many cases, the heterogeneously catalyzed (meth)acrolein partial oxidation to (meth)acrylic acid will be executed with an inert gas volume ratio (l (STP)) of (meth)acrolein to oxygen to steam present in the reaction gas input mixture of 1:(1 to 3):(0 to 20):(3 to 30), preferably of 1:(1 to 3):(0.5 to 10):(7 to 10).

Useful inert diluent gases (these are gases or mixtures of those gases which, in single pass of the reaction gas mixture through the catalyst bed (e.g. a fixed catalyst bed), are preserved chemically unchanged to an extent of at least 95 mol %, preferably to an extent of at least 97 mol % or to an extent of at least 99 mol %, and at best to an extent of 100 mol %) include nitrogen, carbon dioxide, carbon monoxide, noble gases, propane, ethane, methane, butane and/or pentane (i.e. each as a sole diluent gas or in a mixture with one other inert diluent gas or with a plurality of other inert diluent gases among these). The reaction temperatures in such a heterogeneously catalyzed (meth)acrolein partial oxidation are typically in the range from 200 to 400° C., generally from 220 to 380° C., in many cases from 230 to 350° C., frequently from 245 to 285° C. or from 245 to 265° C. The working pressure (absolute pressure) is normally 101.3 to 350 kPa, or 101.3 to 250 kPa, or 101.3 to 205 kPa (especially as the input pressure into the fixed catalyst bed). The (meth)acrolein partial oxidation with the catalysts obtainable in accordance with the invention can of course also be performed at working pressures below atmospheric pressure.

The (meth)acrolein conversion, based on a single pass of the reaction gas mixture through the fixed catalyst bed, is typically at least 90 mol %, frequently at least 98 mol %, and in many cases at least 99 mol %, or even at least 99.9 mol %.

Otherwise, the inventive partial oxidation process can be executed in a manner entirely corresponding to the teachings of DE 10 2007 019 597 A or of WO 2008/104577, or of WO 2011/134932.

More particularly, the source used for the (meth)acrolein required for the inventive partial oxidation may directly be the (meth)acrolein-comprising product gas mixture of a heterogeneously catalyzed partial oxidation of a $C_3/C_4$ precursor compound (for example propene or isobutene) of (meth)acrolein to (meth)acrolein, without any need to remove the (meth)acrolein from such a product gas mixture beforehand.

The (meth)acrylic acid can be removed from the product gas mixture of the partial oxidation in a known manner, for example by first converting the (meth)acrylic acid to the condensed phase by absorptive and/or condensative measures. Subsequent thermal separation processes, such as rectification and/or crystallization, can subsequently isolate (meth)acrylic acid in any purity from the condensed phase (cf. DE 602004924 T and WO 2006/114428 and the prior art cited in these documents).

The present invention further provides catalytically active multielement oxides comprising the elements Mo, W, V, Cu and optionally Sb, wherein the ratio of the elements conforms to the general formula (I)

$$Mo_{12}W_aV_bCu_cSb_d \qquad (I)$$

where a=0.4 to 5.0, preferably 0.6 to 3.5, more preferably 0.8 to 2.5, most preferably 1.0 to 2.0, b=1.0 to 6.0, preferably 1.5 to 5.5, more preferably 2.0 to 5.0, most preferably 2.5 to 4.5, c=0.2 to 1.8, preferably 0.4 to 1.6, more preferably 0.6 to 1.4, most preferably 0.8 to 1.2, and d=0.0 to 2.0, preferably 0.1 to 1.6, more preferably 0.2 to 1.2, most preferably 0.3 to 0.8, and the molar proportion of the element Mo in the total amount of all non-oxygen elements is from 5 to 95 mol %, preferably from 10 to 90 mol %, more preferably from 15 to 85 mol %, most preferably from 20 to 80 mol %, obtainable by one of the aforementioned processes, wherein the BET surface area of the catalytically active multielement oxide is from 16 to 35 m²/g, preferably from 17 to 32 m²/g, more preferably from 18 to 29 m²/g, most preferably from 19 to 26 m²/g.

The stoichiometric efficient a of the element W in the general formula (I) is preferably 0.6 to 3.5, more preferably 0.8 to 2.5, most preferably 1.0 to 2.0.

The stoichiometric efficient b of the element V in the general formula (I) is preferably 1.5 to 5.5, more preferably 2.0 to 5.0, most preferably 2.5 to 4.5.

The stoichiometric efficient c of the element Cu in the general formula (I) is preferably 0.4 to 1.6, more preferably 0.6 to 1.4, most preferably 0.8 to 1.2.

The stoichiometric efficient d of the element Sb in the general formula (I) is preferably 0.1 to 1.6, more preferably 0.2 to 1.2, most preferably 0.3 to 0.8.

The molar proportion of the element Mo in the total amount of all non-oxygen elements is preferably from 10 to 90 mol %, more preferably from 15 to 85 mol %, most preferably from 20 to 80 mol %.

The BET surface area of the catalytically active multielement oxide is preferably from 17 to 32 m²/g, more preferably from 18 to 29 m²/g, most preferably from 19 to 26 m²/g.

Catalytically active multielement oxides as used for the oxidation of acrolein to acrylic acid are typically not in a form with all the metallic elements present therein in the maximum oxidation states thereof. What are meant by maximum oxidation states of the metallic elements are the maximum oxidation states in which the respective elements typically exist in their oxides. The maximum oxidation states of the relevant elements are V(V), Mo(VI), W(VI), Cu(II) and Sb(V).

For example, vanadium may not or not completely be in the V(V) oxidation state, but may also, for example, be in the V(IV) or V(III) oxidation state or in mixed oxidation states. It is possible that a portion of the vanadium is in the V(V) oxidation state and another portion in the V(IV) oxidation state, or a portion of the vanadium is in the V(IV) oxidation state and another portion in the V(III) oxidation state.

It is also possible for other metallic elements in the mixed metal oxides to be in different oxidation states. The oxidation states of the other relevant elements are, for example, Cu(I), Mo(V), Mo(IV) and Sb(III).

In principle, delocalized states may be conceivable when a relatively high electron mobility has the effect that it is possible to distinguish between non-discrete metal atoms having different oxidation states.

Without wishing to enter into any further theoretical interpretations here, the catalytically active multielement oxides can be analyzed by redox titrimetry after digestion in aqueous solution. The content of oxidizable electrons is determined quantitatively by means of titration with KMnO₄ as oxidizing agent. For this purpose, the catalytically active multielement oxides are used directly in powder form prior to application to a shaped support body.

Catalytically active multielement oxides having a defined ratio R of oxidizable electrons to vanadium have particularly advantageous properties in the oxidation of acrolein to acrylic acid. The ratio R is $R=e/CV$ where e is the specific content of oxidizable electrons per g [mol/g] and CV is the specific content of vanadium per g [mol/g].

The ratio R is preferably 1.0 to 2.0, more preferably 1.1 to 1.9, most preferably 1.2 to 1.8.

Titration with KMnO₄ as oxidizing agent is conducted as follows:

15 ml of 96% by weight sulfuric acid, 15 ml of water and 10 ml of 85% by weight phosphoric acid are introduced into a long-neck flask on a stirred hotplate and purged with argon to free them of air. 100 to 200 mg of sample is weighed into a weighing boat and rinsed with water into the long-neck flask. The flask is heated to boiling under an argon atmosphere until the volume of the solution has been concentrated to 40 ml and the sample has dissolved completely (about 30 to 45 minutes depending on the amount of water required).

The solution is then transferred into a titration vessel equipped with a combined Pt electrode and a potentiograph, for example of the Titrando 808 type (Metrohm AG, Herisau, Switzerland). The titrations are conducted at 80° C. under an argon atmosphere. The sample is titrated with aqueous KMnO₄ solution (0.02 mol/l) until the color turns red-violet (excess of KMnO₄). During the titration, the combined Pt electrode is used to measure and record the electrochemical potential.

The titration curve should show a turning point. No point of inflection means that no oxidizable electrons are present. The volume of aqueous KMnO₄ solution at the end point is read off from the titration curve.

The specific content of oxidizable electrons e is $e=(V*C*5)/EW$ where V is the volume of aqueous KMnO₄ solution [I], C is the concentration of aqueous KMnO₄ solution [mol/l] and z is the weight of sample [g].

In some cases, the titration curve may show multiple turning points. This means that there are electrons with different oxidation potentials. Two turning points are possibly an indication of the presence of V(III) and V(IV). FIG. 6 shows a titration curve with two turning points. FIG. 7 shows a titration curve with one turning point.

The present invention further provides processes for producing an eggshell catalyst, wherein a catalytically active multielement oxide of the invention and optionally binders are applied to the outer surface of a geometric shaped support body.

The present invention further provides eggshell catalysts consisting of a geometric shaped support body and a catalytically active multielement oxide of the invention and optionally binders that have been applied to the outer surface of the geometric shaped support body.

The present invention further provides processes for preparing acrylic acid by gas phase catalytic oxidation of acrolein over a fixed catalyst bed, wherein the fixed catalyst bed comprises a catalytically active multielement oxide of the invention or an eggshell catalyst of the invention.

Figure 1:
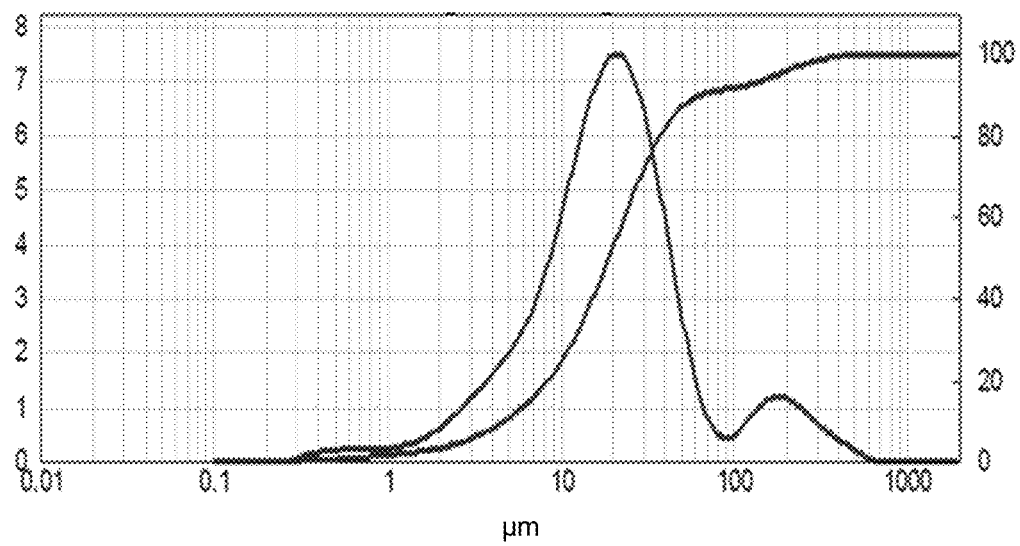
FIG. 1 shows the particle size distribution of powder P in example 22.

Thus, the present invention encompasses especially the following embodiments of the invention:
1. A process for producing a catalytically active multielement oxide comprising the elements Mo, W, V, Cu and optionally Sb, wherein the ratio of the elements conforms to the general formula (I)

$$Mo_{12}W_aV_bCu_cSb_d \qquad (I)$$

where
a=0.4 to 5.0,
b=1.0 to 6.0,
c=0.2 to 1.8 and
d=0.0 to 2.0,
and the molar proportion of the element Mo in the total amount of all non-oxygen elements is from 5 to 95 mol %, which comprises
a) using at least one source of the elemental constituents W of the multielement oxide to produce an aqueous solution or aqueous suspension,
b) admixing the aqueous solution or aqueous suspension obtained in a) with sources of the elemental constituents Mo, V and optionally Sb of the multielement oxide,
c) admixing the aqueous solution or aqueous suspension obtained in b) with sources of the elemental constituents Cu and optionally Sb of the multielement oxide,
d) drying the aqueous solution or aqueous suspension obtained in c) and optionally comminuting to produce a powder P,
e) optionally using the powder P obtained in d), optionally with addition of one or more shaping auxiliaries and after homogeneous mixing, to obtain geometric shaped precursor bodies from the resulting mixture, and
f) subjecting the powder P obtained in d) or the geometric shaped precursor bodies obtained in e) to thermal treatment to form the catalytically active multielement oxide,
wherein the aqueous solution or aqueous suspension used in d) comprises from 1.6% to 5.0% by weight of W and from 7.2% to 26.0% by weight of Mo, based in each case on the total amount of aqueous solution or aqueous suspension.
2. The process according to embodiment 1, wherein the stoichiometric coefficient a of the element W in the general formula (I) is from 0.6 to 3.5.
3. The process according to embodiment 1 or 2, wherein the stoichiometric coefficient a of the element W in the general formula (I) is from 0.8 to 2.5.
4. The process according to any of embodiments 1 to 3, wherein the stoichiometric coefficient a of the element W in the general formula (I) is from 1.0 to 2.0.
5. The process according to any of embodiments 1 to 4, wherein the stoichiometric coefficient b of the element V in the general formula (I) is from 1.5 to 5.5.
6. The process according to any of embodiments 1 to 5, wherein the stoichiometric coefficient b of the element V in the general formula (I) is from 2.0 to 5.0.
7. The process according to any of embodiments 1 to 6, wherein the stoichiometric coefficient b of the element V in the general formula (I) is from 2.5 to 4.5.
8. The process according to any of embodiments 1 to 7, wherein the stoichiometric coefficient c of the element Cu in the general formula (I) is from 0.4 to 1.6.
9. The process according to any of embodiments 1 to 8, wherein the stoichiometric coefficient c of the element Cu in the general formula (I) is from 0.6 to 1.4.
10. The process according to any of embodiments 1 to 9, wherein the stoichiometric coefficient c of the element Cu in the general formula (I) is from 0.8 to 1.2.
11. The process according to any of embodiments 1 to 10, wherein the stoichiometric coefficient d of the element Sb in the general formula (I) is from 0.1 to 1.6.
12. The process according to any of embodiments 1 to 11, wherein the stoichiometric coefficient d of the element Sb in the general formula (I) is from 0.2 to 1.2.
13. The process according to any of embodiments 1 to 12, wherein the stoichiometric coefficient d of the element Sb in the general formula (I) is from 0.3 to 0.8.
14. The process according to any of embodiments 1 to 13, wherein the molar proportion of the element Mo in the total amount of all non-oxygen elements is from 10 to 90 mol %.
15. The process according to any of embodiments 1 to 14, wherein the molar proportion of the element Mo in the total amount of all non-oxygen elements is from 15 to 85 mol %.
16. The process according to any of embodiments 1 to 15, wherein the molar proportion of the element Mo in the total amount of all non-oxygen elements is from 20 to 80 mol %.
17. The process according to any of embodiments 1 to 16, wherein the aqueous solution or aqueous suspension obtained in c) is dried and comminuted in d).
18. The process according to any of embodiments 1 to 16, wherein the aqueous solution or aqueous suspension obtained in c) is spray-dried in d).
19. The process according to any of embodiments 1 to 18, wherein the powder P obtained in d) is used to produce geometric shaped precursor bodies in e).
20. The process according to any of embodiments 1 to 18, wherein the powder P obtained in d), with addition of one or more shaping auxiliaries and after homogeneous mixing, is used in e) to obtain geometric shaped precursor bodies from the resulting mixture.
21. The process according to any of embodiments 1 to 20, wherein the aqueous solution or aqueous suspension used in d) comprises from 1.9% to 5.2% by weight of W.
22. The process according to any of embodiments 1 to 21, wherein the aqueous solution or aqueous suspension used in d) comprises from 2.1% to 4.5% by weight of W.
23. The process according to any of embodiments 1 to 22, wherein the aqueous solution or aqueous suspension used in d) comprises from 2.3% to 3.8% by weight of W.
24. The process according to any of embodiments 1 to 23, wherein the aqueous solution or aqueous suspension used in d) comprises from 8.7% to 22.0% by weight of Mo.
25. The process according to any of embodiments 1 to 24, wherein the aqueous solution or aqueous suspension used in d) comprises from 10.1% to 18.0% by weight of Mo.
26. The process according to any of embodiments 1 to 25, wherein the aqueous solution or aqueous suspension used in d) comprises from 11.5% to 15.0% by weight of Mo.
27. The process according to any of embodiments 1 to 26, wherein water-soluble salts are used as the source of the elemental constituents Mo, W and V.
28. The process according to any of embodiments 1 to 27, wherein admixing is effected in b) with at least one source of the elemental component Sb of the multielement oxide.

29. The process according to any of embodiments 1 to 28, wherein admixing is effected in c) with at least one source of the elemental component Sb of the multielement oxide.
30. The process according to any of embodiments 1 to 29, wherein admixing is effected in b) with at least one source of the elemental component Ta, Cr, Ce, Ni, Co, Fe, Mn, Zn, Nb, Bi, Li, Na, K, Rb, Cs, Mg, Ca, Sr, Ba, Si, Al, Ti or Zr of the multielement oxide.
31. The process according to any of embodiments 1 to 30, wherein admixing is effected in c) with at least one source of the elemental component Ta, Cr, Ce, Ni, Co, Fe, Mn, Zn, Nb, Bi, Li, Na, K, Rb, Cs, Mg, Ca, Sr, Ba, Si, Al, Ti or Zr of the multielement oxide.
32. The process according to any of embodiments 1 to 31, wherein water-soluble salts are used as the source of the elemental constituents Sb.
33. The process according to any of embodiments 1 to 32, wherein the source of the elemental constituents Cu of the aqueous solution or aqueous suspension obtained in b) is added in solid form.
34. The process according to any of embodiments 1 to 33, wherein an aqueous solution is prepared in b).
35. A catalytically active multielement oxide comprising the elements Mo, W, V, Cu and optionally Sb, wherein the ratio of the elements conforms to the general formula (I)

$$Mo_{12}W_aV_bCu_cSb_d \quad (I)$$

where
a=0.4 to 5.0,
b=1.0 to 6.0,
c=0.2 to 1.8 and
d=0.0 to 2.0,
and the molar proportion of the element Mo in the total amount of all non-oxygen elements is from 5 to 95 mol %, obtainable by a process of embodiments 1 to 34, wherein the BET surface area of the catalytically active multielement oxide is from 16 to 35 m²/g.
36. The catalytically active multielement oxide according to embodiment 35, wherein the stoichiometric coefficient a of the element W in the general formula (I) is from 0.6 to 3.5.
37. The catalytically active multielement oxide according to embodiment 35 or 36, wherein the stoichiometric coefficient a of the element W in the general formula (I) is from 0.8 to 2.5.
38. The catalytically active multielement oxide according to any of embodiments 35 to 37, wherein the stoichiometric coefficient a of the element W in the general formula (I) is from 1.0 to 2.0.
39. The catalytically active multielement oxide according to any of embodiments 35 to 38, wherein the stoichiometric coefficient b of the element V in the general formula (I) is from 1.5 to 5.5.
40. The catalytically active multielement oxide according to any of embodiments 35 to 39, wherein the stoichiometric coefficient b of the element V in the general formula (I) is from 2.0 to 5.0.
41. The catalytically active multielement oxide according to any of embodiments 35 to 40, wherein the stoichiometric coefficient b of the element V in the general formula (I) is from 2.5 to 4.5.
42. The catalytically active multielement oxide according to any of embodiments 35 to 41, wherein the stoichiometric coefficient c of the element Cu in the general formula (I) is from 0.4 to 1.6.
43. The catalytically active multielement oxide according to any of embodiments 35 to 42, wherein the stoichiometric coefficient c of the element Cu in the general formula (I) is from 0.6 to 1.4.
44. The catalytically active multielement oxide according to any of embodiments 35 to 43, wherein the stoichiometric coefficient c of the element Cu in the general formula (I) is from 0.8 to 1.2.
45. The catalytically active multielement oxide according to any of embodiments 35 to 44, wherein the stoichiometric coefficient d of the element Sb in the general formula (I) is from 0.1 to 1.6.
46. The catalytically active multielement oxide according to any of embodiments 35 to 45, wherein the stoichiometric coefficient d of the element Sb in the general formula (I) is from 0.2 to 1.2.
47. The catalytically active multielement oxide according to any of embodiments 35 to 46, wherein the stoichiometric coefficient d of the element Sb in the general formula (I) is from 0.3 to 0.8.
48. The catalytically active multielement oxide according to any of embodiments 35 to 47, wherein the catalytically active multielement oxide comprises at least one of the elements Ta, Cr, Ce, Ni, Co, Fe, Mn, Zn, Nb, Bi, Li, Na, K, Rb, Cs, Mg, Ca, Sr, Ba, Si, Al, Ti or Zr.
49. The catalytically active multielement oxide according to any of embodiments 35 to 48, wherein the molar proportion of the element Mo in the total amount of all non-oxygen elements is from 10 to 90 mol %.
50. The catalytically active multielement oxide according to any of embodiments 35 to 49, wherein the molar proportion of the element Mo in the total amount of all non-oxygen elements is from 15 to 85 mol %.
51. The catalytically active multielement oxide according to any of embodiments 35 to 50, wherein the molar proportion of the element Mo in the total amount of all non-oxygen elements is from 20 to 80 mol %.
52. The catalytically active multielement oxide according to any of embodiments 35 to 51, wherein the BET surface area of the catalytically active multielement oxide is from 17 to 32 m²/g.
53. The catalytically active multielement oxide according to any of embodiments 35 to 52, wherein the BET surface area of the catalytically active multielement oxide is from 18 to 29 m²/g.
54. The catalytically active multielement oxide according to any of embodiments 35 to 53, wherein the BET surface area of the catalytically active multielement oxide is from 19 to 26 m²/g.
55. The catalytically active multielement oxide according to any of embodiments 35 to 54, wherein the ratio R of the catalytically active multielement oxide is from 1.0 to 2.0.
56. The catalytically active multielement oxide according to any of embodiments 35 to 55, wherein the ratio R of the catalytically active multielement oxide is from 1.1 to 1.9.
57. The catalytically active multielement oxide according to any of embodiments 35 to 56, wherein the ratio R of the catalytically active multielement oxide is from 1.2 to 1.8.
58. A process for preparing acrylic acid by gas phase catalytic oxidation of acrolein over a fixed catalyst bed, wherein the fixed catalyst bed comprises a catalytically active multielement oxide according to any of embodiments 35 to 57.
59. The use of a catalytically active multielement oxide according to any of embodiments 35 to 57 as catalysts for the heterogeneously catalyzed partial gas phase oxidation of acrolein to acrylic acid.

60. A process for producing an eggshell catalyst, which comprises applying a catalytically active multielement oxide according to any of embodiments 35 to 57 to the outer surface of a geometric shaped support body.

61. A process for producing an eggshell catalyst, which comprises applying a catalytically active multielement oxide according to any of embodiments 35 to 57 and binder to the outer surface of a geometric shaped support body.

62. The use of a multielement oxide according to any of embodiments 35 to 57 for production of eggshell catalysts.

63. An eggshell catalyst consisting of a geometric shaped support body and a catalytically active multielement oxide according to any of embodiments 35 to 57 applied to the outer surface of the geometric shaped support body.

64. An eggshell catalyst consisting of a geometric shaped support body and a catalytically active multielement oxide according to any of embodiments 35 to 57 and binder applied to the outer surface of the geometric shaped support body.

65. A process for preparing acrylic acid by gas phase catalytic oxidation of acrolein over a fixed catalyst bed, wherein the fixed catalyst bed comprises an eggshell catalyst according to embodiment 63 or 64.

66. The use of an eggshell catalyst according to embodiment 63 or 64 as catalysts for the heterogeneously catalyzed partial gas phase oxidation of acrolein to acrylic acid.

EXAMPLES

Example 1 (Comparative Example)

Annular eggshell catalyst C1 with the catalytically active oxide composition $Mo_{12}W_{12}V_3Cu_{12}O_n$ Production of the eggshell catalyst:

A first solution was prepared from 102.5 g of copper(II) acetate monohydrate (Cu content=32% by weight) and 3180 g of water at 70° C. and stirring for a half-hour.

For a second solution, 900 g of ammonium heptamolybdate tetrahydrate (Mo content=55% by weight) was added to 7066 g of water at 90° C. with stirring. While maintaining the temperature, the mixture was stirred for 5 minutes, 156 g of ammonium metavanadate (V content=42% by weight) was added, and the mixture was stirred for a further 40 minutes. Subsequently, 132 g of ammonium paratungstate heptahydrate (W content=72% by weight) was added and the mixture was stirred for a further 30 minutes. An orange solution was obtained.

Next, the first solution was added to the second solution and the mixture was stirred for 15 minutes. To the resultant solution was added 1530 g of a 25% by weight aqueous $NH_3$ solution, the temperature of which was 25° C. A clear solution having a temperature of about 70° C. and a pH of 8.5 was obtained.

The resultant solution was finally introduced into a Mobile Minor 2000 spray tower with FO A1 spray head (GEA Niro, Soeborg, Denmark) by means of a rotary atomizer at 30 000 rpm. The drying was conducted in a hot air stream at an inlet temperature of 350° C. and an exit temperature of 120° C. The powder was introduced into a ZS1-18 kneader (Coperion Werner & Pfleiderer GmbH & Co. KG; Stuttgart, Germany). The powder was kneaded at ambient temperature together with 100 ml of glacial acetic acid and 200 ml of water at 15 rpm for 30 minutes. Subsequently, the material was extruded (length 1 to 10 cm, diameter 6 mm). The extrudates were dried at 110° C. in an air circulation drying cabinet for 16 hours.

1000 g of the precursor composition taken from the air circulation drying cabinet was calcined batchwise in a rotary furnace (analogously to U.S. Pat. No. 9,149,799 B2). The calcination was conducted under a gas stream composed of air and nitrogen with an oxygen content of 2.3% by volume. The rotary furnace was heated to 400° C. within one hour and kept at that temperature for a further 2 hours. Subsequently, the heating was switched off and the material was cooled to ambient temperature with further rotation.

The material taken from the rotary furnace was subsequently comminuted to a fine powder in a ZM 200 mill (Retsch GmbH, Haan, Germany).

The fine powder was used to coat 1600 g of annular support bodies (external diameter 7 mm, length 3 mm, internal diameter 4 mm, surface roughness Rz 45 μm) of the C 220 steatite type (Ceram Tec GmbH, Plochingen, Germany). The coating was conducted in a Hi-Coater LHC 25/36 mixer (Gebruder Lodige Maschinenbau GmbH, Paderborn, Germany). The mixer was retrofitted for continuous powder dosage. For this purpose, a funnel-shaped vessel was connected via a hose (external diameter 11.1 mm, internal diameter 8 mm) to the drum of the mixer. For coating, 500 g of fine powder was introduced into the funnel-shaped vessel. The dosage was effected by means of 50 ms pressure pulses and a positive pressure of 0.7 bar. During the dosage, the contents of the funnel-shaped vessel were moved by means of an anchor stirrer modified in a V shape (made in-house). Between periods of stirring of 2 s, there were pauses for 1 s.

The binder used was a 25% by weight aqueous solution of glycerol. The solution was metered into the mixer at 3 g/min by means of a two-phase nozzle of the 570 S75 type (Düsen-Schlick GmbH, Coburg, Germany), parallel to the dosage of powder. The powder dosage was 6 cm below the two-phase nozzle and was inclined downward by 40°. The powder was dosed outside the spray cone of the two-phase nozzle. The mixer drum rotated clockwise at 15 rpm. The coating was conducted at 25° C. within 40 minutes. Subsequently, the speed of rotation was lowered to 2 rpm, and drying was effected in an air stream (220 l (STP)/h) at 130° C. for 30 minutes. This was followed by cooling to 25° C. The powder was taken up by the surface of the support bodies. No formation of paired support bodies or agglomeration was observed.

Subsequently, the coated support bodies were freed of adhering glycerol in a UM 400 air circulation drying cabinet (Memmert GmbH & Co. KG, Schwabach, Germany). The coated support bodies were distributed homogeneously over perforated sheets with a layer thickness of 2 cm. The perforated sheets had a thickness of 0.5 cm, an opening ratio of 60% and an area of 35 cm×26 cm. The air circulation drying cabinet was heated to 300° C. at 3 K/minute and kept at that temperature for a further 2 hours. This was followed by cooling to 40 to 50° C. within 2 to 3 hours.

The annular eggshell catalyst C1 had an oxidic active composition content of 20.7% by weight. The BET surface area of the catalytically active multielement oxide was 14 $m^2/g$.

Analysis of the Eggshell Catalyst:

A reaction tube (stainless steel (material 1.4541); external diameter 30 mm; wall thickness 2 mm; internal diameter 26 mm; length 464 cm) was charged from the top downward as follows:

Section 1: length 80 cm
empty tube;

Section 2: length 60 cm
preliminary bed of steatite rings of geometry 7 mm×3 mm×4 mm (external diameter×length×internal diameter; C 220 steatite from Ceram Tec GmbH);
Section 3: length 100 cm
fixed catalyst bed composed of a homogeneous mixture consisting of 20% by weight of steatite rings of geometry 7 mm×3 mm×4 mm (external diameter×length× internal diameter; C 220 steatite from Ceram Tec GmbH) and 80% by weight of the eggshell catalyst;
Section 4: length 200 cm
fixed catalyst bed consisting exclusively of the eggshell catalyst as in section 3;
Section 5: length 10 cm
downstream bed of the same steatite rings as in section 2;
Section 6: length 14 cm
Catalyst base made of stainless steel (material 1.4541) for accommodation of the fixed catalyst bed.

A reaction gas mixture conducted through the respective reaction tube charged as described above, flowing through the reaction tube from the top downward, had the following contents:
4.3% by vol. of acrolein,
0.3% by vol. of propene,
0.2% by vol. of propane,
0.3% by vol. of acrylic acid,
5.1% by vol. of oxygen,
0.4% by vol. of carbon oxides,
7% by vol. of water and
82.3% by vol. of nitrogen.

The feed temperature of the reaction gas mixture (at the inlet into the reaction tube) was 210° C., and the space velocity of acrolein on the fixed catalyst bed (as defined in DE 199 27 624 A) was 80 l (STP)/lh.

Over the length of the reaction tube (apart from the last 10 cm of the empty tube in section 1 and the last 3 cm of the tube in section 6), a stirred and externally electrically heated salt bath (mixture of 53% by weight of potassium nitrate, 40% by weight of sodium nitrite and 7% by weight of sodium nitrate; 50 kg of salt melt) flowed around the reaction tube (the flow rate at the tube was 3 m/s). The salt bath temperature TB (with which the salt bath was supplied) was set in all cases so as to result in an acrolein conversion of 99.3 mol % based on a single pass of the reaction gas mixture through the fixed catalyst bed. Along the reaction tube, there was no change in the salt bath temperature owing to additional heating (the salt bath emitted more heat than was released by the reaction tube to the salt bath).

The selectivity of acrylic acid formation ($S^{AA}$ (mol %)) in this document is understood to mean:

$$S^{AA} = \frac{\text{number of moles of acrolein converted to}}{\text{number of moles of acrolein converted over}-} \times 100.$$

The selectivity of $CO_x$ formation (total combustion) is calculated analogously.

An active composition (catalyst) leading to the same conversion at lower temperature under otherwise unchanged reaction conditions has a higher activity.

The conversion of acrolein ($C^{AC}$ (mol %)) in this document is understood to mean:

$$C^{AC} = \frac{\text{number of moles of acrolein con}-}{\text{number of moles of acrolein used}} \times 100 \text{ mol \%.}$$

Table 1 below shows the results obtained as a function of the eggshell catalyst used after 100 hours of operation.

Example 2 (Comparative Example)

Annular eggshell catalyst C2 with the catalytically active oxide composition $Mo_{12}W_{1.2}V_3Cu_{1.2}O_n$ The procedure was as in example 1. The annular eggshell catalyst C2 had an oxidic active composition content of 15.8% by weight. The BET surface area of the catalytically active multielement oxide was 14.8 $m^2/g$.

Example 3 (Comparative Example)

Annular eggshell catalyst C3 with the catalytically active oxide composition $Mo_{12}W_{1.2}V_3Cu_{2.4}O_n$ The procedure was as in example 1. 205.0 g of copper(II) acetate monohydrate was used rather than 102.5 g of copper (II) acetate monohydrate, and the annular eggshell catalyst C3 had an oxidic active composition content of 20.0% by weight. The BET surface area of the catalytically active multielement oxide was 13.5 m2/g.

Example 4 (Comparative Example)

Annular eggshell catalyst C4 with the catalytically active oxide composition $Mo_{12}W_{1.2}V_3Cu_{1.2}Sb_{0.5}O_n$ The procedure was as in example 1. To the second solution was additionally added 56.5 g of antimony acetate (Sb content=46.3% by weight), and the annular eggshell catalyst C4, however, had an oxidic active composition content of 20.7% by weight. The BET surface area of the catalytically active multielement oxide was 14.0 $m^2/g$. The ratio R was 1.60.

Example 5 (Comparative Example)

Annular eggshell catalyst C5 with the catalytically active oxide composition $Mo_{12}W_{1.2}V_3Cu_{1.2}O_n$ The procedure was as in example 1. No aqueous $NH_3$ solution was added, and the annular eggshell catalyst C5 had an oxidic active composition content of 20.7% by weight. The BET surface area of the catalytically active multielement oxide was 19.3 $m^2/g$. The ratio R was 1.75.

Example 6 (Comparative Example)

Annular eggshell catalyst C6 with the catalytically active oxide composition $Mo_{12}W_{1.2}V_3Cu_{1.2}O_n$ The procedure was as in example 1. For preparation of the second solution, ammonium paratungstate heptahydrate was added first, then ammonium heptamolybdate tetrahydrate, and subsequently ammonium metavanadate. No aqueous $NH_3$ solution was added, and the annular eggshell catalyst C6 had an oxidic active composition content of 21.0% by weight. The BET surface area of the catalytically active multielement oxide was 19.6 $m^2/g$. The ratio R was 1.49.

Example 7

Annular eggshell catalyst WE1 with the catalytically active oxide composition $Mo_{12}W_{1.2}V_3Cu_{1.2}O_n$ The procedure was as in example 1. For preparation of the second solution, ammonium paratungstate heptahydrate was added first and the mixture was stirred for 5 minutes, then ammonium heptamolybdate tetrahydrate was added and the mixture was stirred for a further 10 minutes, and subsequently ammonium metavanadate was added and the mixture was stirred for a further 5 minutes. In addition, the first solution was prepared using 1017 g rather than 3180 g of water, and the second solution was prepared using 2261 g rather than 7066 g of water, i.e. the concentrations of the solutions were increased by a factor of 3.2. No aqueous $NH_3$ solution was added, and the annular eggshell catalyst WE1 had an oxidic active composition content of 20.2% by weight. The BET surface area of the catalytically active multielement oxide was 20.5 $m^2/g$. The ratio R was 1.38.

Example 8

Annular eggshell catalyst WE2 with the catalytically active oxide composition $Mo_{12}W_{1.2}V_3Cu_{1.2}O_n$ The procedure was as in example 7. No first solution was prepared. Copper(II) acetate monohydrate was added in solid form to the second solution, and the annular eggshell catalyst WE2 had an oxidic active composition content of 20.7% by weight. The BET surface area of the catalytically active multielement oxide was 19.6 $m^2/g$.

Example 9

Annular eggshell catalyst WE3 with the catalytically active oxide composition $Mo_{12}W_{1.2}V_3Cu_{1.2}Sb_{0.5}O_n$ The procedure was as in example 7. Additionally added to the second solution was 56.5 g of antimony acetate (Sb content=46.3% by weight). No first solution was prepared. Copper(II) acetate monohydrate was added in solid form to the second solution, and the annular eggshell catalyst WE3 had an oxidic active composition content of 20.6% by weight. The BET surface area of the catalytically active multielement oxide was 17 $m^2/g$. The ratio R was 1.65.

Example 10

Annular eggshell catalyst WE4 with the catalytically active oxide composition $Mo_{12}W_{1.2}V_3Cu_{1.2}O_n$ The procedure was as in example 7. No first solution was prepared. Copper(II) acetate monohydrate was added in solid form to the second solution, and the annular eggshell catalyst WE4 had an oxidic active composition content of 15.0% by weight. The BET surface area of the catalytically active multielement oxide was 21.6 $m^2/g$. The ratio R was 1.43.

Example 11 (Comparative Example)

Annular eggshell catalyst C7 with the catalytically active oxide composition $Mo_{12}W_{1.2}V_3Cu_{0.0}O_n$ The procedure was as in example 10. No copper(II)acetate monohydrate was used, and the annular eggshell catalyst C7 had an oxidic active composition content of 15.3% by weight. The BET surface area of the catalytically active multielement oxide was 23 $m^2/g$. The ratio R was 1.01.

Example 12

Annular eggshell catalyst WE5 with the catalytically active oxide composition $Mo_{12}W_{1.2}V_3Cu_{0.2}O_n$ The procedure was as in example 10. However, 17.1 g of copper(II) acetate monohydrate was used rather than 102.5 g of copper(II) acetate monohydrate, and the annular eggshell catalyst WE5 had an oxidic active composition content of 15.8% by weight. The BET surface area of the catalytically active multielement oxide was 26 $m^2/g$.

Example 13

Annular eggshell catalyst WE6 with the catalytically active oxide composition $Mo_{12}W_{1.2}V_3Cu_{0.4}O_n$ The procedure was as in example 10. However, 34.2 g of copper(II) acetate monohydrate was used rather than 102.5 g of copper(II) acetate monohydrate, and the annular eggshell catalyst WE6 had an oxidic active composition content of 15.5% by weight. The BET surface area of the catalytically active multielement oxide was 23.8 $m^2/g$.

Example 14

Annular eggshell catalyst WE7 with the catalytically active oxide composition $Mo_{12}W_{1.2}V_3Cu_{0.8}O_n$ The procedure was as in example 10. However, 68.3 g of copper(II) acetate monohydrate was used rather than 102.5 g of copper(II) acetate monohydrate, and the annular eggshell catalyst WE7 had an oxidic active composition content of 15.1% by weight. The BET surface area of the catalytically active multielement oxide was 20.1 $m^2/g$. The ratio R was 1.26.

Example 15

Annular eggshell catalyst WE8 with the catalytically active oxide composition $Mo_{12}W_{1.2}V_3Cu_{1.0}O_n$ The procedure was as in example 10. However, 85.4 g of copper(II) acetate monohydrate was used rather than 102.5 g of copper(II) acetate monohydrate, and the annular eggshell catalyst WE8 had an oxidic active composition content of 15.1% by weight. The BET surface area of the catalytically active multielement oxide was 25.9 $m^2/g$. The ratio R was 1.35.

Example 16

Annular eggshell catalyst WE9 with the catalytically active oxide composition $Mo_{12}W_{1.2}V_3Cu_{1.1}O_n$ The procedure was as in example 10. However, 94.0 g of copper(II) acetate monohydrate was used rather than 102.5 g of copper(II) acetate monohydrate, and the annular eggshell catalyst WE9 had an oxidic active composition content of 15.3% by weight. The BET surface area of the catalytically active multielement oxide was 21.4 $m^2/g$. The ratio R was 1.37.

Example 17 (Comparative Example)

Annular eggshell catalyst C8 with the catalytically active oxide composition $Mo_{12}W_{12}V_3Cu_{2.4}O_n$ The procedure was as in example 8. However, 205.0 g of copper(II) acetate monohydrate was used rather than 102.5 g of copper(II) acetate monohydrate, and the annular eggshell catalyst C8 had an oxidic active composition content of 20.0% by weight. The BET surface area of the catalytically active multielement oxide was 12.5 $m^2/g$. The ratio R was 1.85.

Example 18 (Comparative Example)

Annular eggshell catalyst C9 with the catalytically active oxide composition $Mo_{12}W_{1.2}V_3Cu_{1.2}O_n$ The procedure was as in example 1. The second solution was produced using 2261 g rather than 7066 g of water, i.e. the concentrations of the solutions were increased by a factor of 3.2. None of the salts went completely into solution. The annular eggshell catalyst C9 had an oxidic active composition content of 21.0% by weight. The BET surface area of the catalytically active multielement oxide was 14.8 m²/g.

Example 19

Annular eggshell catalyst WE10 with the catalytically active oxide composition $Mo_{12}W_{1.2}V_3Cu_{1.4}O_n$ The procedure was as in example 8. However, 119.6 g of copper(II) acetate monohydrate was used rather than 102.5 g of copper(II) acetate monohydrate, and the annular eggshell catalyst WE10 had an oxidic active composition content of 20.8% by weight. The BET surface area of the catalytically active multielement oxide was 22.8 m2/g.

Example 20

Annular eggshell catalyst WE11 with the catalytically active oxide composition $Mo_{12}W_{1.2}V_3Cu_{1.8}O_n$ The procedure was as in example 8. However, 153.7 g of copper(II) acetate monohydrate was used rather than 102.5 g of copper(II) acetate monohydrate, and the annular eggshell catalyst WE11 had an oxidic active composition content of 21.5% by weight. The BET surface area of the catalytically active multielement oxide was 17.7 m²/g.

Example 21 (Comparative Example)

Annular eggshell catalyst C10 with the catalytically active oxide composition $Mo_{12}W_{1.2}V_3Cu_{2.0}O_n$ The procedure was as in example 8. However, 171.0 g of copper(II) acetate monohydrate was used rather than 102.5 g of copper(II) acetate monohydrate, and the annular eggshell catalyst C10 had an oxidic active composition content of 21.2% by weight. The BET surface area of the catalytically active multielement oxide was 12.0 m²/g.

Example 22 (Comparative Example)

Annular eggshell catalyst BV1 with the catalytically active oxide composition $Mo_{12}W_{1.2}V_3Cu_{1.2}O_n$ A first solution was prepared in a stainless steel vessel having a volume of 920 l and a paddle stirrer. 12.1 kg of copper(II) acetate monohydrate (Cu content=32% by weight) was dissolved in 398 kg of water while stirring at about 25° C. The mixture was stirred for a further hour.

A second solution was prepared in a stainless steel vessel having a volume of 3200 l and a propeller stirrer. To an initial charge of 921 kg of water at 40° C. was added, while stirring, 108.8 kg of ammonium heptamolybdate tetrahydrate (Mo content=55% by weight). The mixture was stirred for 30 minutes while heating to 90° C. Maintaining the temperature, 18.2 kg of ammonium metavanadate (V content=42% by weight) was added to the mixture, which was stirred for a further 40 minutes. Subsequently, 16.1 kg of ammonium paratungstate heptahydrate (W content=72% by weight) was added and the mixture was stirred for a further 30 minutes. An orange solution was obtained. The resultant solution was cooled down to 80° C. The ratio R was 0.59.

Next, the first solution was added to the second solution and the mixture was stirred while maintaining the temperature of 80° C. for 15 minutes. To the resultant solution was added 176 kg of a 25% by weight aqueous $NH_3$ solution, the temperature of which was 25° C. A clear solution having a temperature of about 70° C. and a pH of 8.5 was obtained.

The resultant solution was transferred to a stainless steel vessel having a capacity of 8000 l and a crossbeam stirrer. The solution was heated to 80° C. and finally introduced into an F 15 spray tower (GEA Niro, Soeborg, Denmark) by means of a rotary atomizer at 16 000 rpm. The drying was conducted in a hot air stream at an inlet temperature of 375° C. and an exit temperature of 92° C. The resultant spray powder had the particle size distribution shown in FIG. 1.

The subsequent procedure was as in example 1.

The annular eggshell catalyst BV1 had an oxidic active composition content of 20.1% by weight. The BET surface area of the catalytically active multielement oxide was 15.9 m²/g.

Example 23

Figure 2:
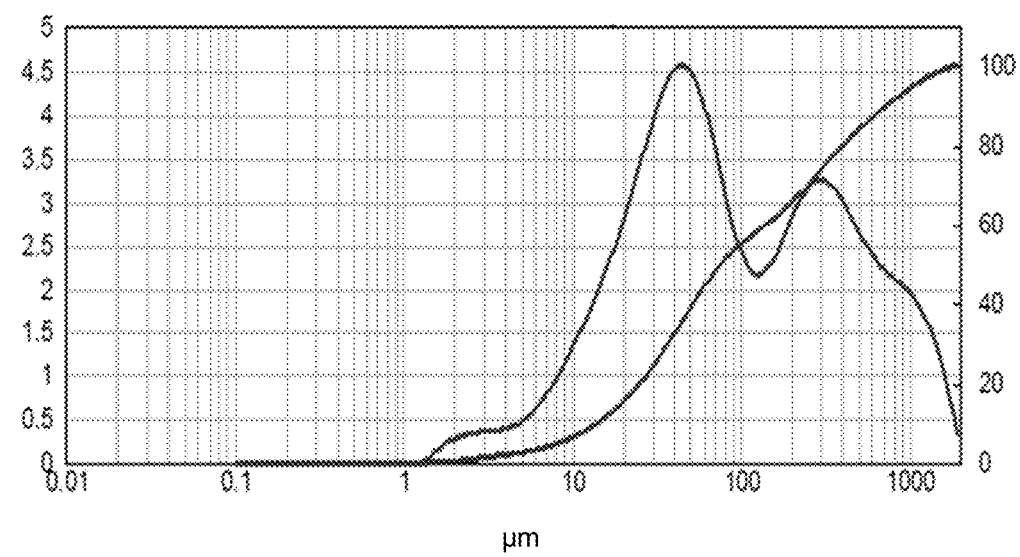
FIG. 2 shows the particle size distribution of powder P in example 23.
Figure 3:
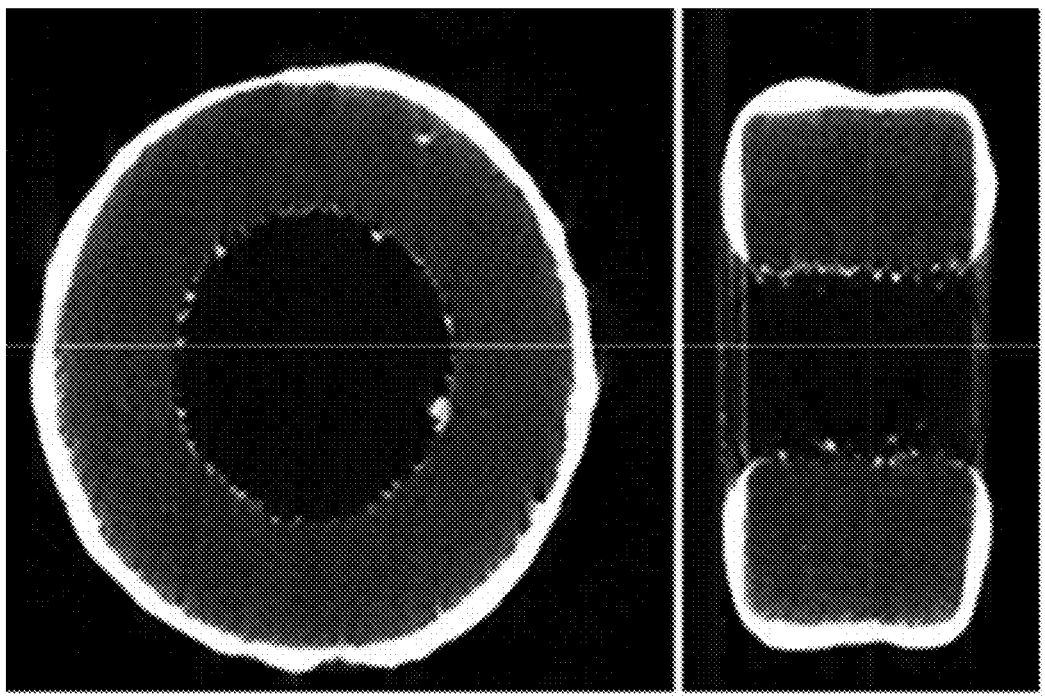
FIG. 3 shows an x-ray microtomography (X-ray μCT) of the annular eggshell catalyst in example 1.
Figure 4:
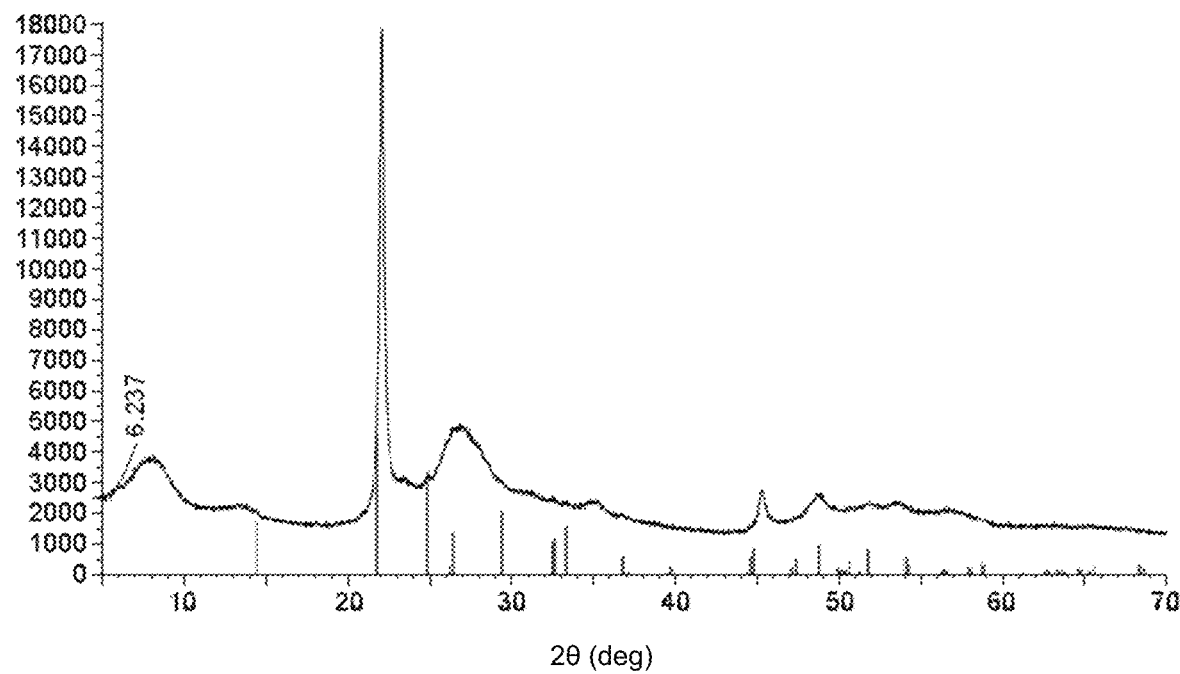
FIG. 4 shows the x-ray diffraction of the annular eggshell catalyst in example 23.
Figure 5:
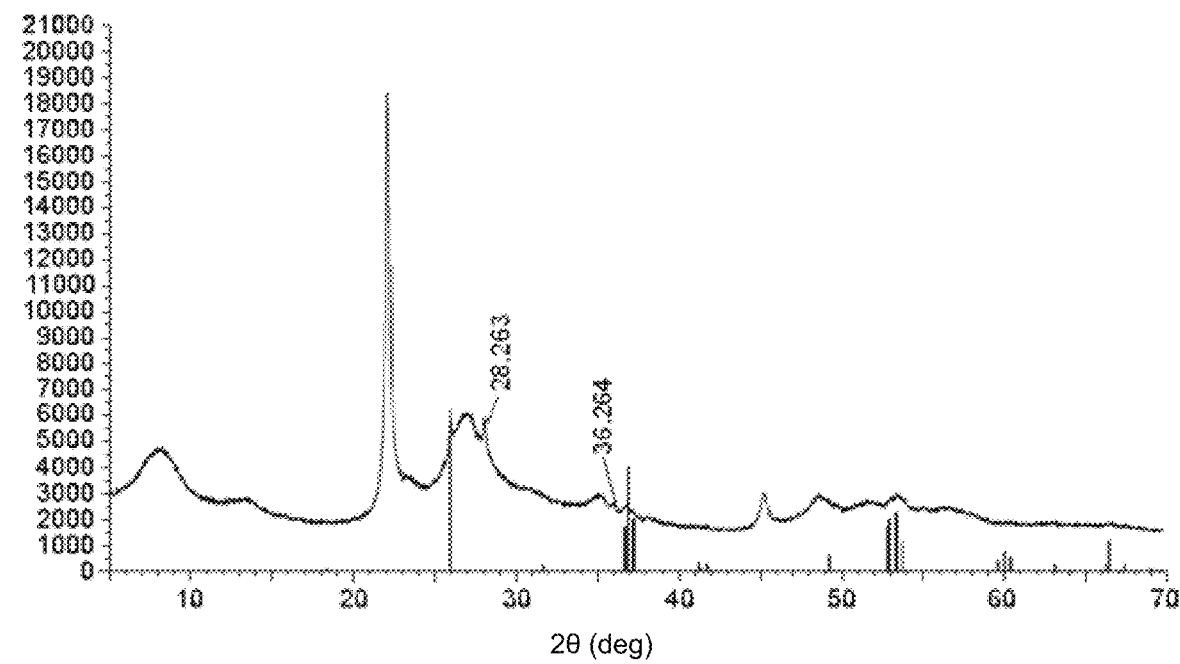
FIG. 5 shows the x-ray diffraction of the annular eggshell catalyst in example 9.
Figure 6:
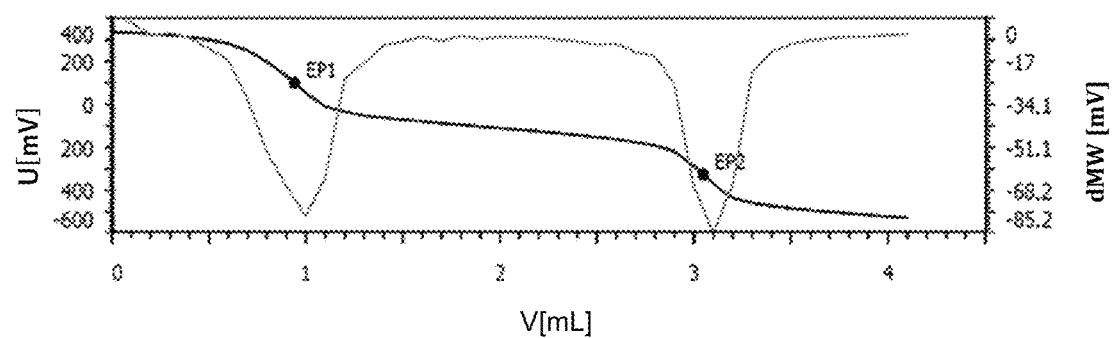
FIG. 6 shows a titration curve of the catalyst in example 9.
Figure 7:
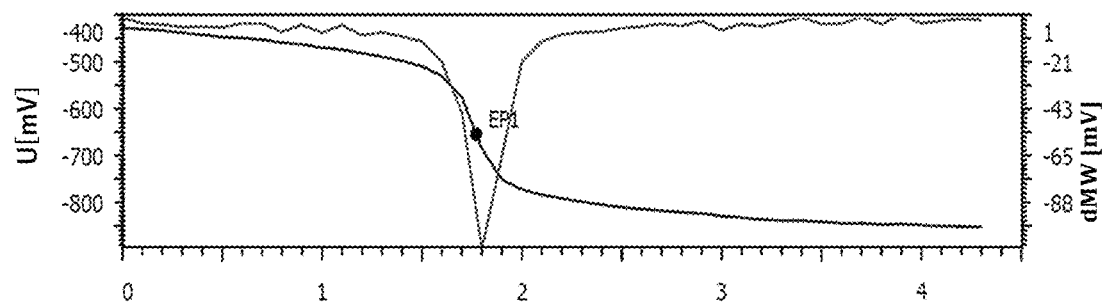
FIG. 7 shows a titration curve of the catalyst in example 22.

Annular eggshell catalyst BV2 with the catalytically active oxide composition $Mo_{12}W_{1.2}V_3Cu_{1.2}O_n$ To an initial charge of 1319 kg of water in a stainless steel vessel having a capacity of 3200 l and a propeller stirrer was added 76 kg of ammonium paratungstate heptahydrate (W content=72% by weight) at 90 to 95° C. while stirring. After 20 minutes, while maintaining the temperature, 513.4 kg of ammonium heptamolybdate tetrahydrate (Mo content=55% by weight) was added to the mixture, which was stirred for a further 10 minutes. Thereafter, 85.9 kg of ammonium metavanadate (V content=42% by weight) was added and the mixture was stirred for a further 10 minutes. An orange solution was obtained. Subsequently, 57.1 kg of copper(II) acetate monohydrate (Cu content=32% by weight) was added and the mixture was stirred for a further 15 minutes. The resultant spray powder had the particle size distribution shown in FIG. 2.

The subsequent procedure was as in example 22.

The annular eggshell catalyst BV2 had an oxidic active composition content of 20.7% by weight. The BET surface area of the catalytically active multielement oxide was 23.2 m2/g.

TABLE 1

Experimental results

| Ex. | Catalyst | AC [% by wt.] | $c_W$ [% by wt.] | $c_{Mo}$ [% by wt.] | TB [° C.] | $S^{COx}$ [mol %] |
|---|---|---|---|---|---|---|
| 1*)**) | $Mo_{12}W_{1.2}V_3Cu_{1.2}O_n$ | 20.7 | 0.73 | 3.79 | 259 | 2.8 |
| 2*)**) | $Mo_{12}W_{1.2}V_3Cu_{1.2}O_n$ | 15.8 | 0.73 | 3.79 | 262 | 2.67 |
| 3*)**) | $Mo_{12}W_{1.2}V_3Cu_{2.4}O_n$ | 20.0 | 0.72 | 3.76 | 259 | 3.3 |
| 4*)**) | $Mo_{12}W_{1.2}V_3Cu_{1.2}Sb_{0.5}O_n$ | 20.7 | 0.72 | 3.77 | 251 | 2.77 |
| 5*)**) | $Mo_{12}W_{1.2}V_3Cu_{1.2}O_n$ | 20.7 | 0.82 | 4.29 | 246 | 3.28 |
| 6*) | $Mo_{12}W_{1.2}V_3Cu_{1.2}O_n$ | 21.0 | 0.82 | 4.29 | 245 | 3.24 |

TABLE 1-continued

Experimental results

| Ex. | Catalyst | AC [% by wt.] | $c_W$ [% by wt.] | $c_{Mo}$ [% by wt.] | TB [° C.] | $S^{COx}$ [mol %] |
|---|---|---|---|---|---|---|
| 7 | $Mo_{12}W_{1.2}V_3Cu_{1.2}O_n$ | 20.2 | 2.08 | 10.84 | 246 | 2.66 |
| 8 | $Mo_{12}W_{1.2}V_3Cu_{1.2}O_n$ | 20.7 | 2.68 | 13.94 | 246 | 2.61 |
| 9 | $Mo_{12}W_{1.2}V_3Cu_{1.2}Sb_{0.5}O_n$ | 20.6 | 2.63 | 13.72 | 246 | 2.66 |
| 10 | $Mo_{12}W_{1.2}V_3Cu_{1.2}O_n$ | 15.0 | 2.68 | 13.94 | 253 | 2.64 |
| 11*) | $Mo_{12}W_{1.2}V_3Cu_{0.0}O_n$ | 15.3 | 2.76 | 14.35 | 259 | 5.74 |
| 12 | $Mo_{12}W_{1.2}V_3Cu_{0.2}O_n$ | 15.8 | 2.74 | 14.28 | 250 | 3.63 |
| 13 | $Mo_{12}W_{1.2}V_3Cu_{0.4}O_n$ | 15.5 | 2.73 | 14.21 | 245 | 4.12 |
| 14 | $Mo_{12}W_{1.2}V_3Cu_{0.8}O_n$ | 15.1 | 2.70 | 14.07 | 246 | 2.85 |
| 15 | $Mo_{12}W_{1.2}V_3Cu_{1.0}O_n$ | 15.1 | 2.69 | 14.01 | 246 | 2.87 |
| 16 | $Mo_{12}W_{1.2}V_3Cu_{1.1}O_n$ | 15.3 | 2.68 | 13.97 | 253 | 2.65 |
| 17*) | $Mo_{12}W_{1.2}V_3Cu_{2.4}O_n$ | 20.0 | 2.60 | 13.55 | 262 | 3.3 |
| 18*)**) | $Mo_{12}W_{1.2}V_3Cu_{1.2}O_n$ | 21.0 | 2.68 | 13.94 | 254 | 2.95 |
| 19 | $Mo_{12}W_{1.2}V_3Cu_{1.4}O_n$ | 20.8 | 2.66 | 13.87 | 244 | 3.17 |
| 20 | $Mo_{12}W_{1.2}V_3Cu_{1.8}O_n$ | 21.5 | 2.64 | 13.74 | 246 | 3.12 |
| 21*) | $Mo_{12}W_{1.2}V_3Cu_{2.0}O_n$ | 21.2 | 2.63 | 13.67 | 254 | 3.1 |
| 22*)**) | $Mo_{12}W_{1.2}V_3Cu_{1.2}O_n$ | 20.1 | 0.70 | 3.63 | 259 | 2.65 |
| 23 | $Mo_{12}W_{1.2}V_3Cu_{1.2}O_n$ | 20.7 | 2.73 | 14.07 | 246 | 2.8 |

*)noninventive
**)metering sequence noninventive
$c_W$ concentration of element W in the solution
$c_{Mo}$ concentration of element Mo in the solution
AC active composition
TB salt bath temperature (acrolein conversion of 99.3 mol %)
$S^{COx}$ $CO_x$ selectivity (total combustion)

The invention claimed is:

1. A process for producing a catalytically active multielement oxide comprising the elements Mo, W, V, Cu and optionally Sb, wherein the ratio of the elements conforms to the general formula (I)

$$Mo_{12}W_aV_bCu_cSb_d \qquad (I)$$

where
a=0.4 to 5.0,
b=1.0 to 6.0,
c=0.2 to 1.8 and
d=0.0 to 2.0,
and the molar proportion of the element Mo in the total amount of all non-oxygen elements is from 5 to 95 mol %, which comprises a) using at least one source of the elemental constituents W of the multielement oxide to produce an aqueous solution or aqueous suspension,
b) admixing the aqueous solution or aqueous suspension obtained in a) with sources of the elemental constituents Mo, V and optionally Sb of the multielement oxide,
c) admixing the aqueous solution or aqueous suspension obtained in b) with sources of the elemental constituents Cu and optionally Sb of the multielement oxide,
d) drying the aqueous solution or aqueous suspension obtained in c) and optionally comminuting to produce a powder P,
e) optionally using the powder P obtained in d), optionally with addition of one or more shaping auxiliaries and after homogeneous mixing, to obtain geometric shaped precursor bodies from the resulting mixture, and
f) subjecting the powder P obtained in d) or the geometric shaped precursor bodies obtained in e) to thermal treatment to form the catalytically active multielement oxide,
wherein the aqueous solution or aqueous suspension used in d) comprises from 1.6% to 5.0% by weight of W and from 7.2% to 26.0% by weight of Mo, based in each case on the total amount of aqueous solution or aqueous suspension.

2. The process according to claim 1, wherein the aqueous solution or aqueous suspension obtained in c) is spray-dried in d).

3. The process according to claim 1, wherein the stoichiometric coefficient a of the element W in the general formula (I) is from 1.0 to 2.0 and/or the stoichiometric coefficient b of the element V in the general formula (I) is from 2.5 to 4.5.

4. The process according to claim 1, wherein the aqueous solution or aqueous suspension used in d) comprises from 2.3% to 3.8% by weight of W and/or comprises from 11.5% to 15.0% by weight of Mo, based in each case on the total amount of aqueous solution or aqueous suspension.

5. The process according to claim 1, wherein water-soluble salts are used as the source of the elemental constituents Mo, V and/or W.

6. The process according to claim 1, wherein the stoichiometric coefficient c of the element Cu in the general formula (I) is from 0.8 to 1.2.

7. The process according to claim 1, wherein admixing is effected in b) or in c) with at least one source of the elemental constituents Sb of the multielement oxide.

8. A catalytically active multielement oxide comprising the elements Mo, W, V, Cu and optionally Sb, wherein the ratio of the elements conforms to the general formula (I)

$$Mo_{12}W_aV_bCu_cSb_d \qquad (I)$$

where
a=0.4 to 5.0,
b=1.0 to 6.0,
c=0.2 to 1.8 and
d=0.0 to 2.0,
and the molar proportion of the element Mo in the total amount of all non-oxygen elements is from 5 to 95 mol %, obtained by the process of claim 1, wherein the BET surface area of the catalytically active multielement oxide is from 16 to 35 m²/g.

9. The catalytically active multielement oxide according to claim 8, wherein the stoichiometric coefficient a of the element W in the general formula (I) is from 1.0 to 2.0 and/or the stoichiometric coefficient b of the element V in the general formula (I) is from 2.5 to 4.5.

10. The catalytically active multielement oxide according to claim 8, wherein the BET surface area of the catalytically active multielement oxide is from 19 to 26 m²/g.

11. The catalytically active multielement oxide according to claim 8, wherein the stoichiometric coefficient c of the element Cu in the general formula (I) is from 0.8 to 1.2.

12. The catalytically active multielement oxide according to claim 8, wherein the catalytically active multielement oxide comprises the element Sb.

13. A process for producing an eggshell catalyst, which comprises applying a catalytically active multielement oxide according to claim 8 and optionally binder to the outer surface of a geometric shaped support body.

14. An eggshell catalyst consisting of a geometric shaped support body and the catalytically active multielement oxide according to claim 8 and optionally binder applied to the outer surface of the geometric shaped support body.

15. A process for preparing acrylic acid by gas phase catalytic oxidation of acrolein over a fixed catalyst bed, wherein the fixed catalyst bed comprises the catalytically active multielement oxide according to claim 8.

* * * * *